United States Patent
Rolland et al.

(10) Patent No.: US 6,184,037 B1
(45) Date of Patent: *Feb. 6, 2001

(54) CHITOSAN RELATED COMPOSITIONS AND METHODS FOR DELIVERY OF NUCLEIC ACIDS AND OLIGONUCLEOTIDES INTO A CELL

(75) Inventors: Alain Rolland; Russell J. Mumper, both of The Woodlands, TX (US)

(73) Assignee: Genemedicine, Inc., The Woodlands, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/850,597

(22) Filed: May 2, 1997

Related U.S. Application Data

(60) Provisional application No. 60/018,342, filed on May 17, 1996.

(51) Int. Cl.$^7$ .......................... A01N 43/04; A61K 31/70; C07H 21/00; C08B 37/08
(52) U.S. Cl. .............................. 435/455; 514/44; 514/55; 536/20; 536/23.1
(58) Field of Search ................................ 435/72, 74, 84, 435/91.1, 101, 325, 375, 455, 459; 514/44, 23, 25, 42, 54, 55; 536/20, 23.1, 24.5; 935/52, 54; 106/162.2; 524/716

(56) References Cited

U.S. PATENT DOCUMENTS

| | | | |
|---|---|---|---|
| 3,922,260 | 11/1975 | Peniston et al. | 536/20 |
| 4,046,750 | 9/1977 | Rembaum | 526/310 |
| 5,364,791 | 11/1994 | Vegeto et al. | 435/320.1 |
| 5,498,421 | * 3/1996 | Grinstaff et al. | 424/450 |
| 5,639,473 | * 6/1997 | Grinstaff et al. | 424/450 |

FOREIGN PATENT DOCUMENTS

| | | |
|---|---|---|
| 9009780 | 9/1990 | (WO) . |
| 9318759 | 9/1993 | (WO) . |
| 96/00295 | 1/1996 | (WO) . |
| 96/21470 | 7/1996 | (WO) . |

OTHER PUBLICATIONS

Derwent Publications Ltd., *Database WPI*, Section Ch, Week 9141, Class B04, AN 91–299437 (abstract for JP 890336384) (1991).

Ishimori, "Immobilization of gene on negative charge carrier," *Chemical Abstracts* 117(1): abstract no. 2175 (1992).

Mao et al., "DNA–chitosan nanospheres: derivatization and storage stability," *Proc. Int. Symp. Controlled Release Bioact. Mater .* 24:671–672 (1997).

Mumper et al., "Novel polymeric condensing carriers for gene delivery," *Proc. Int. Symp. Controlled Release Bioact. Mater .* 22:178–179 (1995).

Murata, et al., "The molecular design of quaternary chitosan conjugate for gene delivery having recognition ability," *Chemical Abstracts* 126(12) abstract no. 153349 (1997).

Murata, et al., "Possibility of application of quaternary chitosan having pendant galactose residues as gene delivery tool," *Carbohydrate Polymers* 29(1):69–74 (1996).

Alexakis et al., *Applied Biochemistry and Biotechnology* 50:93–106 (1995).

Bailey, in *Techniques in Protein Chemistry*, Elsevier, Amsterdam, The Netherlands, pp. 348–349 (1967).

Chandy and Sharma, "Chitosan—as a Biomaterial," *Biomat. Art. Cells, Art. Org.* 18(1):1–24 (1990).

Curotto and Aros, "Quantitative Determination of Chitosan and the Percentage of Free Amino Groups," *Analytical Biochemistry* 211:240–241 (1993).

Domard and Cartier, "Glucosamine oligomers: 1. Preparation and Characterization," *Int. J. Biol. Macromol.* 11:297–302 (1989).

Fulton et al., "Luminescent Reporter Gene Assays for Luciferase and β–galactosidase Using a Liquid Scintillation Counter," *BioTechniques* 14(5):762–763 (1993).

Imai et al., "Interaction of indomethacin with low molecular weight chitosan, and improvements of some pharmaceutical properties of indomethacin by low molecular weight chitosans," *International Journal of Pharmacetuics* 67:11–20 (1991).

Kristl et al., "Hydrocolloids and gels of chitosan as drug carriers," *International Journal of Pharmaceutics* 99:13–19 (1993).

Meshali and Gabr, "Effect of interpolymer complex formation of chitosan with pectin or acacia on the release behaviour of chlorpromazine HCl," *International Journal of Pharmaceutics* 89:177–181 (1993).

Mumper et al., *Proceed. Intern. Symp. Control. Rel. Bioact. Mater.* 22:178–179 (1995).

Nagai et al., "Application of Chitin and Chitosan to Pharmaceutical Preparations," in *Chitin, Chitosan, and Related Enzymes*, Academic Press, New York, pp. 21–39 (1984).

Nguyen et al., "Firefly Luciferase Luminescence Assays Using Scintillation Counters for Quantitation in Transfected Mammalian Cells," *Analytical Biochemistry* 171:404–408 (1988).

Patent application No. 08/584,043, titled "Lipophilic Peptides For Macromolecule Delivery", filed on Jan. 11, 1995.

(List continued on next page.)

Primary Examiner—George C. Elliott
Assistant Examiner—Thomas G Larson
(74) Attorney, Agent, or Firm—Lyon & Lyon LLP

(57) ABSTRACT

Compositions of chitosan-based compounds and nucleic acid or oligonucleotide which are capable of delivery to a cell. Methods of preparation of the compositions. Methods of administering the compositions in vitro to cells in culture or in vivo to an organism.

23 Claims, 9 Drawing Sheets

OTHER PUBLICATIONS

Rios et al., "Counterion Binding to Cationic Polyelectrolytes in Aqueous Solution," *Journal of Polymer Sciences: Part B: Polymer Physics* 29:805–809 (1991).

Shaper et al, "Male Germ Cell Expression of Murine β4–Galactosyltransferase: A 796–base pair genomic region containing two cAMP–responsive elements (CRE)–like elements, mediates male germ cell–specific expression in transgenic mice," *J. Biol. Chem.* 269:25165–25171 (1994).

Shirashi et al., "Controlled Release of Indomethacin by Chitosan–Polyelectrolyte Complex: Optimization and in Vivo/In Vitro Evaluation," *Journal of Controlled Release* 25:217–225 (1993).

Skaugrud, "Chitosan Makes the Grade,"*Manufacturing Chemist* pp. 31–35 (Oct. 1989).

Smith et al., "Nucleic Acid Transporters for Delivery of Nucleic Acids into a Cell," U.S. Patent Application Serial No. 08/484,777, filed Dec. 18, 1995.

Srinivasan and Kamalam, "Polyelectrolyte Complexes of Glycol Chitosan with Some Polysaccharides. I. Mixing Ratio and Dielectric Propertiesm," *Biopolymers* 21:251–263 (1982).

Takahashi et al., "Characterics of Polyion Complexes of Chitosan with Sodium Alginate and Sodium Polyacrylate," *International Journal of Pharmaceutics* 61:35–41 (1990).

Takayama et al., "Effect of Interpolymer Complex Formation on Bioadhesive Property and Drug Release Phenomenon of Compressed Tablet Consisting of Chitosan and Sodium Hyaluronate," *Chem. Pharm. Bull.* 38:1993–1997 (1990).

Uglea and Dumitriu–Medvichi, "Medical Applications of Synthetic Oligomers," in *Polymeric Biomaterials*, edited by Severian Dumitriu, Marcel Dekker, Inc. (1993).

Vegeto, U.S. Application, Serial No. 07/939,246, entitled "Mutated Steriod Hormone Receptors, Methods for Their Use and Molecular Switch for Gene Therapy," filed Sep. 2, 1992.

Vengerov and Semenov, "Electron Microscopy of DNA Complexes with Synthetic Oligopeptides," *Electron Microsc. Rev.* 5:193–207 (1992).

Wagner et al., "Transferrin–polycation–DNA complexes: The effect of polycations on the structure of the complex and DNA delivery to cells," *Proc. Natl. Acad. USA* 88:4255–4259 (1991).

Young et al., "Selective Inactivation of Eukaryotic β–Galactosidase in Assays for Inhibitors of HIV–1 TAT Using Bacterial β–Galactosidase as a Reporter Enzyme," *Analytical Biochemistry* 215:24–30 (1993).

Ouchi and Banba, "Antitumor Activity of Chitosan and Chitin Immobilized 5–Fluorouracils through Hexamethylene Spacers via Carbamoyl Bonds," *Journal of Bioactive and Compatible Polymers* 4:362–371 (1989).

Ouchi et al., "Design of Chitosan—5FU Conjugate Exhibiting Antitumor Activity," *J. Macromol. Sci.—Chem.* A28(10):959–975 (1991).

Ouchi et al., "Synthesis and antitumor activity of chitosan carrying 5–fluorouracils," *Makromol. Chem.* 190:1817–1825 (1989).

\* cited by examiner

CHITOSAN RELATED COMPOSITIONS AND METHODS FOR DELIVERY OF NUCLEIC ACIDS AND OLIGONUCLEOTIDES INTO A CELL

CROSS-REFERENCE TO RELATED APPLICATIONS

This application claims the benefit of Mumper and Rolland, U.S. Provisional Application 60/018,342, entitled "Chitosan Related Compositions and Methods for Delivery of Nucleic Acids and Oligonucleotides into a Cell", filed May 17, 1996. This application is also related to Rolland and Mumper, U.S. patent application Ser. No. 08/372,213 entitled, "Formulated Nucleic Acid Compositions and Methods of Administering the Same for Gene Therapy," filed Jan. 13, 1995. These applications are hereby incorporated herein by reference in their entireties, including any drawings and figures.

FIELD OF INVENTION

This invention relates generally to the fields of gene delivery and gene expression. In particular, it relates to the delivery of nucleic acids and oligonucleotides to cells using non-viral methods.

BACKGROUND OF THE INVENTION

The following description of the background of the invention is provided to aid in understanding the claimed invention, but it is not admitted to constitute or describe prior art to the claimed invention and should in no way be construed as limiting the claimed invention.

Chitin, the chemical structure of which is shown in FIG. 1, is the main constituent in the shells of crustaceans and is the most abundant naturally occurring biopolymer other than cellulose. Chitosan, the chemical structure of which is also shown in FIG. 1, is derived from chitin and can be formed by deacetylation of chitin. Chitosan is commercially available in a wide variety of molecular weights (i.e., 10–1,000 kDa) and usually has a degree of deacetylation ranging between 70% and 90%.

Chitosan has been reported to form compositions with a variety of anionic drugs and polyanions such as indomethacin, polyacrylate, pectin, acacia, alginate, hyaluronate, and some polysaccharides (J. Kristl et al., *Hydrocolloids and Gels of Chitosan as Drug Carriers. Int. J. Pharm.*, 99; 13–19 (1993); S. Shiraishi et al., *Controlled Release of Indomethacin by Chitosan-Polyelectrolyte Complex: Optimization and In Vivo/In Vitro Evaluation. J. Contr. Rel.*, 25; 217–225(1993); M. M. Meshali and K. E. Gabr. *Effect of Interpolymer Complex Formation of Chitosan with Pectin or Acacia on the Release Behavior of Chlorpromazine HCl. Int. J. Pharm.*, 89; 177–181(1993); T. Nagai et al., *Application of Chitin and Chitosan to Pharmaceutical Preparations.* In: "Chitin, Chitosan, and Related Enzymes." Academic Press, New York, 1984, 21–39; H. E. Rios et al., *Counterion Binding to Cationic Polyelectrolytes in Aqueous Solution. J. Polym. Sci., Polym. Phys.* 29; 805–809(1991); T. Takahashi et al., *Characteristics of Polyion Complexes of Chitosan with Sodium Alginate and Sodium Polyacrylate. Int. J. Pharm.*, 61; 35–41(1990); K. Takayama et al., *Effect of Interpolymer Complex Formation on Bioadhesive Property and Drug Release Phenomenon of Compressed Tablets Consisting of Chitosan and Sodium Hyaluronate. Chem. Pharm. Bull.*, 38; 1993–1997(1990); R. Srinivasan and R. Kamalam. *Polyelectrolyte Complexes of Glycol-Chitosan with Some Polysaccharides. I. Mixing Ratio and Dielectric Properties. Biopolymers,* 21; 251–263(1982).

These polyelectrolyte compositions with chitosan have been well characterized in terms of optimal complexation conditions (i.e., ionic strength, pH, temperature, and ratios of components), composition morphology, and composition stability. Chitosan has also been proposed for use as a biomedical membrane, artificial skin, for delivery of anticancer drugs to tumor cells, and as a pharmaceutical delivery system for prescription drugs. In addition, chitosan has been shown to be biodegradable, biocompatible, to have very low toxicity, and no thrombogenic activity.

The use of chitosan as a component of a complex in a non-viral gene delivery system in an in vitro use is described in Mumper et al., *Proceed. Intern. Symp. Control. Rel. Bioact. Mater.*, 22:178–179, 1995, incorporated herein by reference in its entirety, including any drawings and figures. Chitosan is described as effective in condensing negatively charged plasmid DNA due to charge interactions with the positively charged chitosan. Mumper et al., report on the correlation between physicochemical properties of the gene transfer complexes and their in-vitro transfection efficiency. Specifically, they report that the use of smaller molecular weight chitosan as a component of the delivery system (i.e., chitosan in the range of 2–4 kDa M.W.) results in the smallest particle of the gene delivery system and also in an increased transfection of cells with the condensed delivery system.

Chitosan has also been used with a pharmacologically active compound such as insulin in the form of a solution or as a coating on polystyrene microspheres. These formulations involved the use of chitosan of molecular weights of 10,000 or greater, preferably at least 100,000 or 200,000 and most preferably about 500,000. The chitosan/insulin formulations were prepared by mixing equal volumes of insulin and chitosan in solution. The formulation was administered nasally to rats via microsyringe. These formulations have been reported as disclosed in WO 90/09780.

The use of chitosan in microspheres containing naked DNA has been reported by Alexakis et al., *Applied Biochemistry and Biotechnology,* 50:93–106, 1995, incorporated herein by reference in its entirety, including any drawings and figures. The immobilized DNA within chitosan-coated alginate microspheres was designed to test the role of metabolic byproducts of digestion in promoting damage to DNA. The microspheres were designed to pass through the digestive system without being taken up by cells in the animal. Upon excretion, the intact microsphere can be recovered and the DNA examined to asses the role of metabolic byproducts of digestion in promoting cancer through damage to nucleic acid. The microspheres were designed to retain the DNA within their core during transit through the animal. The microsphere prevented access to DNA from hydrolytic enzymes but allowed metabolic byproducts of digestion to cross or exit the microsphere shell. The reported recovery rate of the microspheres after administration was 97%. According to the abstract, leakage of DNA from intact microspheres was not observed.

SUMMARY OF THE INVENTION

The invention features compositions of chitosan-based compounds and nucleic acids or oligonucleotides. The compositions are capable of non-viral gene delivery (i.e., delivery of nucleic acid without the use of any genomic viral components) via various routes of administration. The invention also features methods for the preparation of chitosan-based compositions and methods for the introduction of the compositions into a cell for expression of nucleic acids, oligonucleotides or gene products transported by the composition. The compositions are useful for enhancing the administration to, and uptake of, nucleic acids or oligonucleotides by an organism. The compositions are also useful for in vitro transfections and in vivo gene delivery, and among other things for the administration of proteins, polypeptides, or peptides encoded by the nucleic acid or oligonucleotide.

An efficient strategy for enhancing nucleic acid delivery in vivo is to present, at the target site, nucleic acid in composition of sufficient size to promote its cellular uptake. The compositions of the present invention, which are designed to administer nucleic acid into a cell, comprise a substance which promotes condensation of nucleic acid when the substance is complexed with the nucleic acid. The resulting composition is capable of increasing the efficacy of transfecting cells in an organism or cells in vitro cell culture.

Chitosan's properties are useful in complexing and condensing nucleic acids or complexing oligonucletides. DNA, which is a polyanionic nucleic acid has a high net negative charge due to the presence of two phosphate moieties on each base pair. Therefore, DNA is an excellent candidate for complexation with chitosan and chitosan oligomers for non-viral gene delivery. Neutralization of the negative charge of DNA by the amine groups of chitosan and chitosan oligomers results in condensation of DNA into a compact particle which protects the DNA from nuclease degradation and delivers the DNA, either specifically or non-specifically, to target cells.

Chitosan has structural characteristics similar to glycosamino-glycans (GAGs) and appears to mimic their function (T. Chandy and C. P. Sharma. *Chitosan—As a Biomaterial. Biomat., Art. Cells, Art. Org.,* 18; 1–24(1990). GAGs are widely distributed among various tissues and, like heparin sulphate proteoglycans (GAGS), may be a component of cell membranes. Thus, chitosan may provide natural targeting to cell surfaces (e.g., endothelial cells). For example, chitin and chitosan have been reported to selectively distribute to the surface of tumor cells (T. Ouchi and T. Banba. *Fixation of 5-Fluorouracil to Chitosan and its Antitumor Activity. Trans. Soc. Biomat.* 11; 232(1988). A summary of the beneficial properties of chitin, chitosan, and chitosan oligomers for gene and oligonucleotide delivery is shown in Table 1.

TABLE 1

Summary of the Beneficial Properties of Chitosan and Chitosan Oligomers for Gene and Oligonucleotide Delivery Natural Polymers
Low cost and commercially available
Different molecular weights, degrees of deacetylation available
Chitosan can be de-polymerized to well defined oligomers
Biodegradable and biocompatible
Low toxicity
No thrombogenicity
Mimic function of glycosamino-glycans
Approved orally as food additives
Mucosal bioadhesive Thus, in one aspect, the invention features a composition capable of delivering a nucleic acid or an oligonucleotide to a cell. The composition includes a chitosan-based compound and a nucleic acid or an oligonucleotide.

By "composition" is meant any product resulting after mixing a nucleic acid or an oligonucleotide with a chitosan-based compound.

In preferred embodiments, the compositions are suitable for in vivo delivery of a nucleic acid or oligonucleotide, and are "pharmaceutical compositions". Such compositions produce a physiological effect when administered to an organisms, and preferably produce a therapeutic effect. Also preferably, the compositions are suitable for internal administration. Such pharmaceutical compositions include a nucleic acid or oligonucleotide and a chitosan-based compound, and preferably also include one or more other pharmaceutically acceptable components. Such components can, for example, include pharmaceutically acceptable carriers and solutes.

By "mixing" is meant an intermingling or physical mixture of substances. In a preferred embodiment the nucleic acid or oligonucleotide is added by mixing to the chitosan-based compound. In a more preferred embodiment the chitosan-based compound is added by mixing to the nucleic acid or oligonucleotide. In a most preferred embodiment the pH of the chitosan-based compound is adjusted before mixing with the nucleic acid or oligonucleotide which has been separately adjusted for pH.

The chitosan, chitin, or chitosan oligomer is preferably bound to the nucleic acid or oligonucleotide noncovalently. The composition preferably has a diameter between 15 nm and 10,000 nm, more preferably between 15 nm and 1,000 nm, and even more preferably between 15 and 500 nm. The composition preferably has a net positive charge ratio and a pH in the range of 4.0 to 8.0 (more preferably between 5.0 and 7.0, even more preferably between 5.5 and 6.5). The composition preferably does not contain any of the following: carbonyl iron powder, hexamethylene diisocyanate or gluteraldehyde as described in Alexakis et al., *Applied Biochemistry and Biotechnology,* 50:93–106, 1995, incorporated herein by reference in its entirety, including any drawings and figures.

The molecular weight of the composition preferably is within the range of 5 kDA to 1,000 kDA, more preferably between 5 kDA and 600 kDA, even more preferably between 5 kDA and 250 kDA. By "molecular weight" is meant, as is commonly understood in the art, the relative mass of a molecule or compound in relation to that of a Hydrogen atom. In a preferred embodiment, the molecular weight of compositions is determined by gel permeation chromatography.

The composition is preferably capable of delivering the nucleic acid or oligonucleotide into a cell. By "delivering the nucleic acid or oligonucleotide into a cell" is meant transporting a complexed and condensed nucleic acid or a complexed oligonucleotide in a stable and condensed state through the membrane of a cell (in vitro or in vivo), thereby transferring the nucleic acid or oligonucleotide from the exterior side of the cell membrane, passing through the lipid bilayer of the cell membrane and subsequently into the interior of the cell on the inner side (i.e., cytosol side) of the cell membrane and releasing the nucleic acid or oligonucleotide once within the cellular interior. The phrase "delivering the nucleic acid or oligonucleotide into a cell" is also meant to exclude the type of transport and/or diffusional loss of DNA as described in Alexakis et al., *Applied Biochemistry and Biotechnology,* 50:93–106, 1995, incorporated herein by reference in its entirety, including any drawings and figures.

In a preferred embodiment at least 1% of the nucleic acid or oligonucleotide in the composition is delivered into the cell. In a more preferred embodiment, at least 10% of the nucleic acid or oligonucleotide is delivered into the cell. In an even more preferred embodiment, at least 50% of the nucleic acid or oligonucleotide is delivered into the cell. In a most preferred embodiment, at least 90% of the nucleic acid or oligonucleotide is delivered into the cell.

Furthermore, the composition may prevent lysosomal degradation of the nucleic acid by endosomal lysis. In addition, although not necessary, the composition may also efficiently transport the nucleic acid through the nuclear membrane into the nucleus of a cell.

By "chitosan-based compound" is meant any compound having the polysaccharide chemical structure shown in FIG. 1 as common to chitosan and chitin. Chitosan is a linear polysaccharide composed of two monosaccharides: N-acetyl-D-glucosamine and D-glucosamine linked together by B(1–4) glycosidic bonds (FIG. 1). Chitosan is derived from chitin (poly-N-acetyl-D-glucosamine). Chitin is deacetylated to chitosan by the treatment of strong NaOH at elevated temperatures with the material being kept in the solid phase to gain the highest possible yield (O. Skaugrud. *Chitosan Makes the Grade. Manufacturing Chemist*, October (1989) 31–35). The term "chitosan based compound" includes chitin, chitosan, chitosan oligomers, as well as derivatives or analogues thereof that are capable of forming suitable compositions in combination with a nucleic acid or an oligonucleotide.

By "analogs" or "derivatives thereof" are meant chitosan-based compounds having: (i) specific or non-specific cell targeting moieties that can be covalently attached to chitin, chitosan, and chitosan oligomers or ionically or hydrophobically adhered to a chitosan-based compound complexed with a nucleic acid or an oligonucleotide, and (ii) various derivatives or modifications of chitin, chitosan, and chitosan oligomers which serve to alter their physical, chemical, or physiological properties. Examples of analogs include, but are not limited to, chitosan-based compounds having specific or non-specific targeting ligands, membrane permeabilization agents, sub-cellular localization components, endosomolytic (lytic) agents, nuclear localization signals, colloidal stabilization agents, agents to promote long circulation half-lives in blood, and chemical derivatives such as salts, O-acetylated and N-acetylated derivatives, etc. These analogs can be formed by covalent attachment, derivatization, or modification to the complexing agents directly, adhered to complex particles by ionic or hydrophobic interaction, or simply physically combined with the complexing agents or their complex particles. Examples of such analogs include, but are not limited to, agents such as a lipophilic peptide binding molecule or JTS-1 or a derivative as a lysis agent as described in patent application Ser. No. 08/584,043, entitled "Lipophilic Peptides For Macromolecule Delivery", filed on Jan. 11, 1995, incorporated by reference herein in its entirety including any drawings or figures. In a preferred embodiment some sites for chemical modification of chitosan include: $C_2$ (NH—CO—CH$_3$ or NH$_2$), $C_3$ (OH), or $C_6$ (CH$_2$OH).

By "nucleic acid" is meant both RNA and DNA including: cDNA, genomic DNA, plasmid DNA, antisense molecule, polynucleotides or olignucleotides, RNA or mRNA. In a preferred embodiment, the nucleic acid administered is plasmid DNA which comprises a "vector". By "vector" is meant a nucleic acid molecule incorporating sequences encoding polypeptide product(s) as well as, various regulatory elements for transcription, translation, transcript stability, replication, and other functions as are known in the art and as described herein. Vector can include expression vector. An "expression vector" is a vector which allows for production or expressing a product encoded for by a nucleic acid sequence contained in the vector. The product may be a protein or a nucleic acid such as an mRNA which can function as an antisense molecule. A "transcript stabilizer" is a sequence within the vector which contributes to prolonging the half life (slowing the elimination) of a transcript.

A "DNA vector" is a vector whose native form is a DNA molecule. By "non-viral" is meant any vector or composition which does not contain genomic material of a viral particle. An "antisense molecule" can be a mRNA or an oligonucleotide which forms a duplex with a complementary nucleic acid strand and can prevent the complementary strand from participating in its normal function within a cell. For example, expression of a particular growth factor protein encoded by a particular gene. A "gene product" means products encoded by the vector. Examples of gene products include mRNA templates for translation, ribozymes, antisense RNA, proteins, glycoproteins, lipoproteins and phosphoproteins. "Post-translational processing" means modifications made to the expressed gene product. These may include addition of side chains such as carbohydrates, lipids, inorganic or organic compounds, the cleavage of targeting signals or propeptide elements, as well as the positioning of the gene product in a particular compartment of the cell such as the mitochondria, nucleus, or membranes. The vector may comprise one or more genes in a linear or circularized configuration. The vector may also comprise a plasmid backbone or other elements involved in the production, manufacture, or analysis of a gene product. The nucleic acid may be associated with a targeting ligand to effect targeted delivery.

A "targeting ligand" is a component of the delivery system or vehicle which binds to receptors, with an affinity for the ligand, on the surface or within compartments of a cell for the purpose of enhancing uptake or intracellular trafficking of the vector. Glucans such as Tris-galactosyl residues, carnitine derivatives, mannose-6-phosphate, monoclonal antibodies, peptide ligands, and DNA-binding proteins represent examples of targeting ligands which can be used to enhance uptake. "Intracellular trafficking" is the translocation of the vector within the cell from the point of uptake to the nucleus where expression of a gene product takes place. Alternatively, cytoplasmic expression of a nucleic acid construct utilizing, for example, a T7 polymerase system may be accomplished. Various steps in intracellular trafficking include endosomal release and compartmentalization of the vector within various extranuclear compartments, and nuclear entry. "Endosomal release" is the egress of the vector from the endosome after endocytosis. This is an essential and potentially rate limiting step in the trafficking of vectors to the nucleus. A lytic peptide may be used to assist in this process. A "lytic peptide" is a peptide which functions alone or in conjunction with another compound to penetrate the membrane of a cellular compartment, particularly a lysosomal or endosomal compartment, to allow the escape of the contents of that compartment to another cellular compartment such as the cytosolic and/or nuclear compartment. "Compartmentalization" is the partitioning of vectors in different compartments within a defined extracellular or intracellular space. Significant extracellular compartments may include, for example, the vascular space, hair follicles, interstitial fluid, synovial fluid, cerebral spinal fluid, thyroid follicular fluid. Significant intracellular compartments may include endosome, potosome, lysosome, secondary lysosome, cytoplasmic granule, mitochondria, and the nucleus.

"Nuclear entry" is the translocation of the vector across the nuclear membrane into the nucleus where the gene may be transcribed.

"Elimination" is the removal or clearance of materials (vectors, transcripts, gene products) from a specific compartment over time. This term may be used to reflect elimination from the body, the vascular compartment, extracellular compartments, or intracellular compartments. Elimination includes translocation (excretion) from a particular compartment or biotransformation (degradation).

The compounds which increase the efficacy of transfection of a nucleic acid are suitable for internal administration. By "suitable for internal administration" is meant that the compounds are suitable to be administered within the tissue of an organism, for example within a muscle or within a joint space, intradermally or subcutaneously. Other forms of administration which may be utilized are topical, oral, pulmonary, nasal and mucosal; for example, buccal, vaginal or rectal. These substances may be prepared as solutions, suspensions, gels, emulsions or microemulsions. Oil suspensions of lyophilized nucleic acid, such as plasmid DNA may be utilized. Delivery systems for these oil suspensions include, but are not limited to, sesame oil, cottonseed oil, soybean oil, lecithins, Tweens, Spans and Miglyols.

By "solutions" is meant water soluble substances and/or surfactants in solution with nucleic acids. By "suspensions" is meant water insoluble oils containing suspended nucleic acids. By "gels" is meant high viscosity substances containing nucleic acids. By "emulsion" is meant a dispersed system containing at least two immiscible liquid phases. Emulsions usually have dispersed particles in the 0.1 to 100 micron range. They are typically opaque and thermodynamically unstable. Nucleic acids in the water phase can be dispersed in oil to make a w/o emulsion. This w/o emulsion can be dispersed in a separate aqueous phase to yield a w/o/w emulsion. Alternatively, a suitable oil could be dispersed in an aqueous phase to form an o/w emulsion.

A "microemulsion" has properties intermediate to micelles and emulsions and is characterized in that they are homogenous, transparent and thermodynamically stable. They form spontaneously when oil, water, surfactant and co-surfactant are mixed together. Typically, the diameter of the dispersed phase is 0.01 to 0.1 microns, usually of the w/o and o/w type. The sustained-release compound containing a nucleic acid is administered to the tissue of an organism, for example, by injection. In one embodiment the tissue is preferably muscle tissue. In another embodiment the tissue is preferably a joint space.

By "sustained-release compound" is meant a substance with a viscosity above that of an isotonic saline solution (150 mM NaCl) containing a nucleic acid; for example, DNA in saline at 1 mg/ml has a viscosity of 3.01 mPa.sec, DNA in saline at 2 mg/ml has a viscosity of 3.26 mPa.sec, DNA in saline at 3 mg/ml has a viscosity of 5.85 mPa.sec (Viscosity measurements were performed at 25° C. in a Brookfield DV-III Rheometer with a No. 40 Spindle at 75 rpm for 30 minutes). Preferably the sustained-release compound has a viscosity in the range of about 0.1–20,000 mPa.sec above that of a complexation in which isotonic saline is the delivery system for a nucleic acid. More preferably the range is about 0.1–5000 mPa.sec above that of a complexation in which isotonic saline is the carrier for a nucleic acid. Even more preferably the range is about 0.1–1000 mPa.sec above that of a complexation in which isotonic saline is the carrier for a nucleic acid.

"Targeted delivery" involves the use of targeting ligands which specifically enhance translocation of a nucleic acid to specific tissues or cells. A "target" is a specific organ, tissue, or cell for which uptake of a vector and expression of a gene product is intended. "Uptake" means the translocation of the vector from the extracellular to intracellular compartments. This can involve receptor mediated processes, fusion with cell membranes, endocytosis, potocytosis, pinocytosis or other translocation mechanisms. The vector may be taken up by itself or as part of a complex. "Binding" is an intermediate step in uptake of some compositions involving a high-affinity interaction between a targeting ligand and a surface receptor on a target cell.

By "oligonucleotide" is meant a single-stranded polynucleotide chain. In a preferred embodiment, the oligonucleotide is less than 100 residues in length. In a more preferred embodiment, the oligonucleotide is less than 50 residues in length. In a most preferred embodiment, the oligonucleotide is less than 30 residues in length.

In a preferred embodiment, the invention features a composition capable of complexing and condensing the nucleic acid or oligonucleotide. These compositions provide smaller, or condensed, and more stable nucleic acid particles for delivery, thereby enhancing the transfection rate of nucleic acid into the cell and the subsequent expression therein.

By "complexing" is meant a high affinity interaction, based upon non-covalent binding, between the chitosan-based substance and the nucleic acid or oligonucleotide. By "affinity" is meant the selective tendency of elements to combine with one, rather than another element, when the physicochemical conditions are appropriate. This interaction is most preferably an ionic interaction but may be brought about wholly or in part by hydrogen bonding, Van der Walls interactions or other chemical attractions commonly recognized by those in the art. The compounds which complex and condense a nucleic acid may also interact or associate with the nucleic acid by intermolecular forces and/or valence bonds such as: Van der Waals forces, ion-dipole interactions, ion-induced dipole interactions, hydrogen bonds, or ionic bonds.

These interactions may serve the following functions: (1) Stereo selectively protect nucleic acids from nucleases by shielding; (2) facilitate the cellular uptake of nucleic acid by "piggyback endocytosis". By "piggyback endocytosis" is meant the cellular uptake of a drug or other molecule complexed to a delivery system that may be taken up by endocytosis (C. V. Uglea and C. Dumitriu-Medvichi, *Medical Applications of Synthetic Oligomers*. In: "Polymeric Biomaterials." Edited by Severian Dumitriu. Marcel Dekker, Inc. 1993) and incorporated herein by reference including all drawings and figures. To achieve the desired effects set forth, it is desirable, but not necessary, that the substances which condense and complex nucleic acid have amphipathic properties; that is, the substance has both hydrophilic and hydrophobic regions. The hydrophilic region of the substance may associate with the largely ionic and hydrophilic regions of the nucleic acid, while the hydrophobic region of the substance may act to retard diffusion of nucleic acid and to protect nucleic acid from nucleases. Additionally, the hydrophobic region may specifically interact with cell membranes, possibly facilitating endocytosis of the composition and thereby nucleic acid associated with the compound. This chitosan-based composition may increase the pericellular concentration of nucleic acid. Agents which may have amphipathic properties and are generally regarded as being pharmaceutically acceptable are chitin, chitosan, and chitosan oligomers.

By "condensing" is meant charge neutralization, exclusion of water and compacting into colloidal particles. Compositions formed as a result of complexing with chitosan-based compounds are smaller in size than the naked nucleic acids which have not been so treated (e.g., See Example 7 infra). The composition which condense and complex nucleic acid may also achieve one or more of the following effects, due to their physical, chemical or rheological properties: (1) Protect nucleic acid, for example plasmid DNA, from nucleases; (2) increase the area of contact between nucleic acid, such as plasmid DNA, through extracellular matrices and over cellular membranes, into which the nucleic acid is to be taken up; (3) concentrate nucleic acid, such as plasmid DNA, at cell surfaces due to water exclusion; (4) indirectly facilitate uptake of nucleic acid, such as plasmid DNA, either increasing interaction with cellular membranes and/or by perturbing cellular membranes due to osmotic, hydrophobic or lytic effects. The following may be suitable for use as compounds which condense and complex nucleic acid: chitin; chitosan; chitosan oligomers.

By "increase the efficacy of transfection" is meant that a nucleic acid or oligonucleotide when administered to an organism in a composition comprising such a substance will be more readily taken up into the interior of a cell by translocating across the cellular membrane than if administered in a composition without such a substance, for example when administered in a formulation such as a saline solution. The increased efficiency of uptake of nucleic acid, or oligonucleotide into cells could occur, for example, due to a better steric fit between the composition containing the nucleic acid and a pit on the surface of the cellular membrane or due to protection of the nucleic acid from attack by nucleases.

In another preferred embodiment, the composition has a net positive charge ratio. By "net charge" is meant the resulting positive, negative or neutral character of a compound which is determined after balancing the total number of positive and negative charges possessed by a molecule or compound. For example, the DNA molecule, has a net negative charge due to the presence of two anionic phosphate moieties on each base pair of the molecule. The number of negatively charged phosphates exceed in number the total number of positive charges on the DNA molecule. Thus the surfeit of negative charges imparts a net negative character or charge to DNA. The number of negative charges to positive charges on compositions determines the net charge ratio. The net charge ratio is symbolized by (−/+) where a dash, "−", stands for a negative charge and a plus sign, "+", stands for a positive charge. A net charge ratio of 1:1(−/+) is neutral; of 2:1(−/+) is negative and of 1:2(−/+) is positive.

In another preferred embodiment, the composition is suitable for use in vivo or in vitro. By "in vivo" is meant in a living organism. By "in vitro" is meant any method of maintaining cells in a living or potentially living state while outside of a living organism. Various methods of in vitro culture are well known to those skilled in the art. In vitro encompass as within this meaning techniques described as ex vivo. Ex vivo means techniques in which cells can be co-transfected with a composition containing nucleic acid and also containing a selectable marker. This selectable marker is used to select those cells which have become transformed. It is well known to those skilled in the art the type of selectable markers to be used with transfection studies.

Another embodiment features the composition additionally mixed with a cryoprotectant. By "cryoprotectant" is meant any chemical or compound which will serve to protect nucleic acid and oligonucleotides and the complexed particles during lyophilization, storage, and subsequent rehydration. Examples of "cryoprotectants" include, but are not limited to, such compounds as lactose, sucrose, mannitol, and trehalose.

In another aspect, the nucleic acid or oligonucleotide is delivered to a cell by the step of exposing the composition to the cell. The method may be performed in vitro, in vivo, or on a cell that has been removed from a living organism. If the method is performed in vivo, then the exposing step may be performed by administering the composition to an organism.

By "administering" is meant the route of introduction of the composition into a body. Administration can be directly to a target tissue or through systemic delivery. In particular, administration may be by direct injection to the cells. Routes of administration include, but are not limited to, intramuscular, aerosol, oral, topical, systemic, nasal, ocular, intraperitoneal and/or intratracheal, buccal, sublingual, oral, intradermal, subcutaneous, pulmonary, intra-artricular, and intra-arterial. In a preferred embodiment administration is by intravenous administration.

By "organism" is meant a living entity capable of replication. In a preferred embodiment the organism is an animal, in a more preferred embodiment a mammal, and in a most preferred embodiment a human.

In another aspect the invention provides a method of making the compositions described above. The method involves the steps of exposing the chitosan-based compound to an acid, filtering the acid treated product and adding the acid treated and filtered product to the nucleic acid or oligonucleotide in an acceptable pharmaceutical vehicle.

In an embodiment the molecular weight of the chitin, chitosan, or chitosan oligomer used in the chitosan-based composition is in the range of 5–1000 kDa, in a preferred embodiment in the range of 5–600 kDa, in a more preferred embodiment in the range of 5–250 kDa, in a most preferred embodiment in the range of 5–100 kDa.

The chitin, chitosan, or chitosan oligomer preferably is not used in a chitosan-based composition, as defined herein, which includes a microsphere; either as a part of a microsphere, a coating on a microsphere, or encapsulated within a microsphere. The chitosan-based composition herein preferably does not include in any way, shape, or manner, a microsphere as part of its1 configuration as described in WO 90/09780.

In WO 90/09780 pharmaceutical compositions can be adsorbed to or encapsulated within pre-formed hollow spheres made of cross-linked chitosan of a size measured in microns (i.e., microspheres). The final size of the particles described in WO 90/09780 can be controlled by the initial size of the cross-linked chitosan microsphere to which pharmaceutical compositions are either absorbed or encapsulated. In WO 90/09780 the chitosan microsphere composition cannot condense DNA. However, chitosan-based compositions of the instant application preferably can condense DNA (as the term condensed is defined herein).

The spherically-shaped, chitosan-based compositions described herein, are formed from a solution of chitosan, chitin, or chitosan oligomer mixed with a solution of DNA. These chitosan-based compositions are able to condense DNA. The mixture of DNA and chitosan solution, as described herein, is preferably capable of forming a final composition that can be in the range of 0.015–10.0 microns in size. The size of the DNA/chitosan compositions of the instant invention can be influenced by, but is not limited to, the following: the concentration of DNA, the concentration of chitosan, the method of mixing, the pH, the temperature, and the order of mixing the components of the composition.

The DNA/chitosan compositions of the instant invention have different chemical and physical properties than the microspheres compositions described in WO 90/09780.

In preferred embodiments the nucleic acid or oligonucleotide is present in a concentration ranging from 10 to 4,000 ug per ml of the acceptable pharmaceutical carrier, more preferably in a concentration ranging from 100 to 400 ug per ml of said acceptable pharmaceutical carrier.

The composition preferably has a net positive charge ratio and a pH in the range of 4.0 to 8.0 (more preferably between 5.0 and 7.0, even more preferably between 5.5 and 6.5).

In another embodiment of the invention, the compound which complexes and condenses a nucleic acid is a sustained-release compound which may be administered to an organism or to cells in culture. By "sustained-release" is meant that nucleic acid is made available for uptake by surrounding tissue or cells in culture for a period of time longer than would be achieved by administration of the nucleic acid in a less viscous medium, for example, a saline solution.

In yet another aspect, the composition is administered to an organism. By "administering or administration" is meant the route of introduction of the composition into an organism. Administration can be directly to a target tissue or through systemic delivery. Administration can include but is not limited to: oral, subcutaneous, intradermal, intramuscular, rectal, intravenous, intra tumoral, pulmonary, nasal, intra articular, ocular, topical, and intra-osseous methods of delivery. In particular, the present invention can be used for administering nucleic acid for expression of specific nucleic acid sequence in cells. Routes of administration include intramuscular, aerosol, olfactory, oral, topical, systemic, ocular, intraperitoneal and/or intratracheal. A preferred method of administering is by oral delivery.

In addition, another means to administer the chitosan-based compositions of the present invention is by using a dry powder form for inhalation. Furthermore, administration may also be by aerosolization with a nebulizer mist and thereby inhaled. The specific delivery route of any selected vector construct will depend on the particular use for the nucleic acid associated with the nucleic acid composition.

In general, a specific delivery approach for each chitosan-based composition used will focus on uptake with regard to the particular targeted tissue, followed by demonstration of efficacy. Uptake studies will include uptake assays to evaluate cellular uptake of the nucleic acid and expression of the specific nucleic acid of choice. Such assays will also determine the localization of the target nucleic acid after uptake, and establishing the requirements for maintenance of steady-state concentrations of expressed protein. Efficacy and cytotoxicity is then tested. Toxicity will not only include cell viability but also cell function. Incorporated DNA into compositions, as described herein, which undergo endocytosis increases the range of cell types that will take up foreign genes. The chosen method of delivery should result in cytoplasmic accumulation and optimal dosing. The dosage will depend on the route of administration but should be between 0.1–1000 mg/kg of body weight/day. This dose is readily determinable by standard methods. It could be more or less depending on the optimal dosing. The duration will extend through the course of administration, possibly continuously. Establishment of levels of expression of the nucleic acid or oligonucleotide within the cell is dependent upon the rate of uptake and degradation. Decreasing the degree of degradation will prolong the intracellular half-life of the nucleic acid or oligonucleotide to be delivered.

In another aspect, the composition is in a pharmaceutically acceptable carrier. By "pharmaceutically acceptable carrier" is meant, but not restricted to any of the following: Methylcelluloses, hydroxypropylcelluloses, hydroxypropylmethylcelluloses; heteropolysaccharides (pectins); poloxamers (Pluronics); poloxamines (Tetronics); ethylene vinyl acetates; polyethylene glycols; polyvinylpyrrolidones; saline; polyvinylalcohols; polyvinylacetates; phosphatidylcholines (lecithins); propylene glycol; miglyols; polylactic acid; polyhydroxybutyric acid; xanthan gum buffers. Also, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

Other and further objects, features, and advantages will be apparent from the following description of the drawings and the presently preferred embodiments of the invention, as well as the examples provided herein.

DESCRIPTION OF THE PREFERRED EMBODIMENTS

Figure 1:
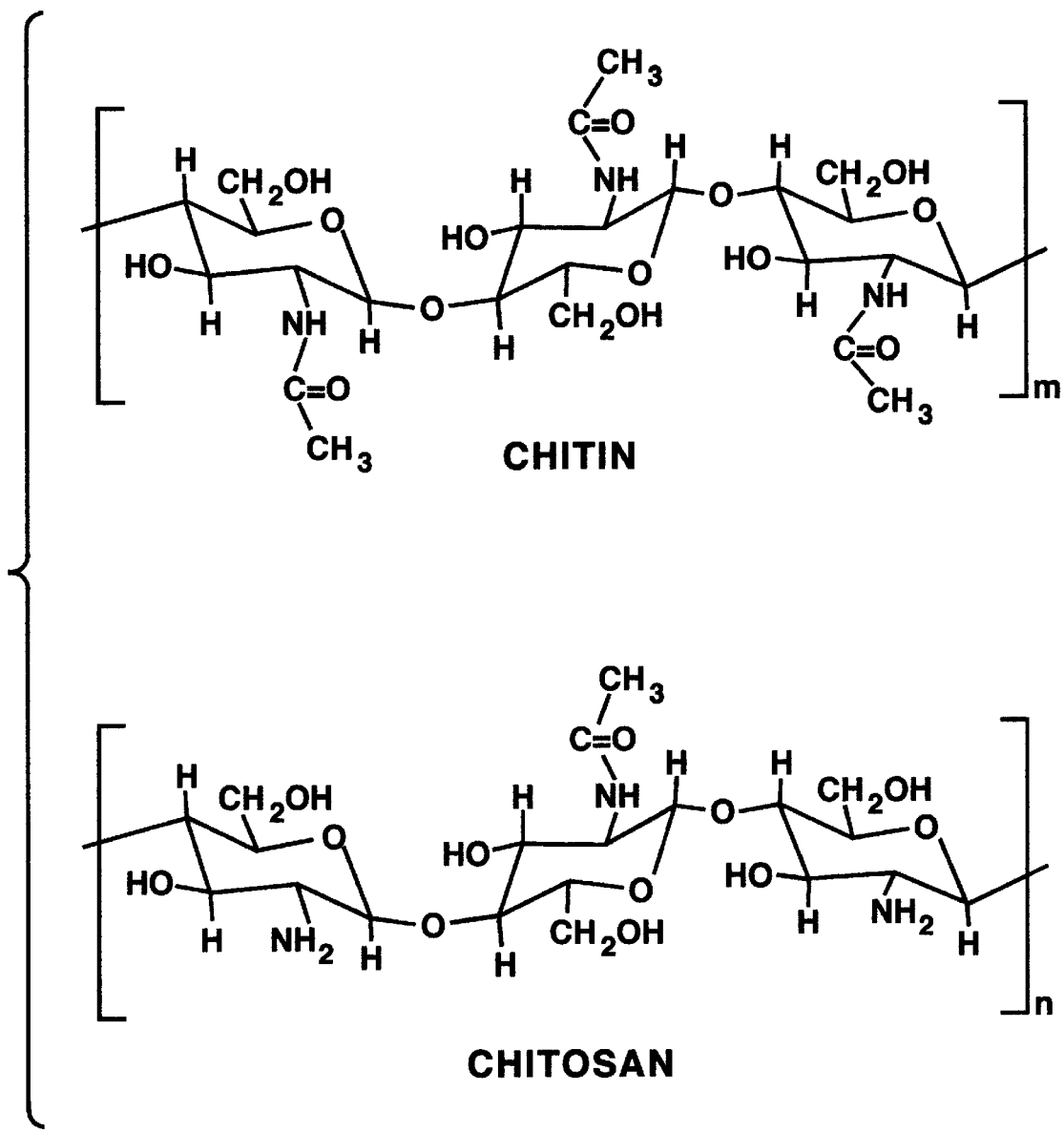
FIG. 1 shows the chemical structures of Chitin (poly-N-acetyl-D-glucosamine) and Chitosan (deacetylated poly-N-acetyl-glucosamine). Some sites for chemical modification of chitosan include: $C_2$ ($NH-CO-CH_3$ or $NH_2$), $C_3$ (OH), or $C_6$ ($CH_2OH$).

The following are preferred embodiments of the present invention using compositions of chitosan-based compounds for delivery of nucleic acid and oligonucleotides to a cell. These embodiments are offered by way of illustration and are not intended to limit the invention in any manner.

I. Theory and Operation of Invention

An important goal of the current invention is to increase the efficacy of gene delivery and gene expression in target cells. Gene delivery is the first step in the process of ultimately obtaining expression of a product encoded by a nucleic acid targeted for delivery to a cell. One method of improving gene delivery is to effect the uptake of nucleic acid by cells. Uptake of nucleic acid by cells is dependent on a number of factors, one of which is the size of the composition carrying the nucleic acid or oligonucleotide to be expressed in the target cell. For instance, some investigators report a positive correlation between the degree of condensation of DNA in a complex to be delivered to a cell and the efficacy of cellular DNA uptake (Wagner et al., *PNAS*, Vol 88, 1991).

Accordingly, it would be desirable to find a substance able to complex and condense nucleic acids, protect them from degradation by nucleases and enable enhanced uptake by the target cell by either non-specific adsorptive mechanisms or receptor mediated endocytosis and also, permit attachment of additional moieties to the composition to enhance the ability of the composition to obtain expression of the product targeted to a cell. Furthermore, these substances should be easily available, biocompatible and capable of being modified to alter their physical, chemical and physiological properties. Such substances should be able to form compositions suitable for administration to an organism by various means such as, but not limited to, injection or oral delivery while maintaining or regaining the physical characteristics necessary to increase cellular uptake and expression of nucleic acids or oligonucleotides.

Chitosan is such a substance. However, the majority of pharmaceutically acceptable chitosan products have molecular weights ranging from 100–1,000 kDa. They have two distinct properties: i) higher molecular weight chitosans are usually only soluble in dilute acid solutions and are insoluble at pH>6.5, and ii) aqueous acidic solutions of these chitosans are quite viscous. The present invention solves these problems by utilizing techniques for reducing the molecular weight of conventional chitosan-based compounds, thereby providing improved solubility and viscosity properties at physiologically relevant pH's.

The embodiments and examples below demonstrate how specific chitosan-based compositions stabilize and condense nucleic acid for cell delivery. Furthermore, these embodiments and examples demonstrate how surface and nuclear ligands can be used with a delivery peptide to target nucleic acid into the cellular interior and/or the cell nucleus. Such targeted delivery can be enhanced by use of a lysis agent and lipophilic peptides. It was found that though in vitro transfection results do not necessarily predict effective in vivo delivery, the chitosan-based compounds can be used in compositions which enhance in vivo delivery, as well as in vitro transfection of nucleic acids. Thus, the embodiments and examples include in vivo and in vitro techniques, various cellular or animal models and methods for inserting nucleic acid into cells.

Also supplied below are embodiments and examples of specific chitosan-based compositions that can be used to provide certain functionalities to the associated nucleic acid in the composition, and thus within a transformed cell or animal containing such a cell. Those in the art will recognize that specific moieties of the chitosan-based compounds can be identified as that containing the functional region providing the desirable properties of the composition. Such regions can be readily minimized using routine deletion, mutation, or modification techniques or their equivalent.

II. Utility of the Invention

The compositions of the present invention enhance delivery of nucleic acid into the cell preferably by delivering stabilized and condensed nucleic acid into the nucleus of the cell. These compositions can be used to treat diseases by enhancing delivery of specific nucleic acid to the appropriately targeted cells. These compositions can also be used to create transformed cells, as well as transgenic animals for assessing human disease in an animal model.

The present invention also features the use of compositions of chitosan-based compound with nucleic acid noncovalently bound to the chitosan-based compound that is capable of condensing the nucleic acid or oligonucleotide. These chitosan-based compounds provide small, condensed compositions, or reduced diameter compositions and more stable nucleic acid particles for delivery, thereby enhancing the transfection efficiency of the nucleic acid into the cell and into the nucleus.

By taking advantage of the characteristics of these compositions, the present invention enhances delivery of nucleic acid to a cell. The components of the compositions can be used alone, together or with other components of a nucleic acid carrier as disclosed in PCT publication WO 93/18759, Woo et al., entitled "A DNA Carrier System and Method of Use," the whole of which (including drawings) is hereby incorporated by reference in its entirety. The chitosan composition, together with lysis or lipophilic peptides can enhance the delivery of nucleic acid to cells by enhancing the release of stable, condensed nucleic acid from an endosome into the cellular interior.

In addition a composition with a chitosan-based compound, nucleic acid, and lysis agent, the present invention also features various compositions which can contain a targeting ligand for a cell surface receptor and a nuclear localization signal as well. The targeting ligands are capable of binding to a cell surface receptor and entering a cell through cytosis (e.g., endocytosis, potocytosis, pinocytosis). By using targeting ligands specific to certain cells, nucleic acid can be delivered using the chitosan-based compositions directly to the desired tissue. The nuclear localization signal are capable of recognizing and transporting nucleic acid through the nuclear membrane to the nucleus of the cell. Such nuclear localization signals help enhance the compositions ability to target nucleic acid to the cell nucleus.

The abilities of the above chitosan-based compositions to deliver nucleic acid to specific cells and to the nucleus also allows transgenic animal models to be used for the dissection of molecular carcinogenesis and disease, assessing potential chemical and physical carcinogens and tumor promoters, exploring model therapeutic avenues as well as livestock agricultural purposes. Furthermore, the above chitosan-based compositions permit methods for administration and treatment of various diseases. In addition, the above chitosan-based compositions can transform cells to produce particular proteins, polypeptides, and/or RNA. Likewise, chitosan-based compositions can be used in vitro with tissue culture cells. In vitro uses allow the role of various nucleic acids to be studied by targeting specific expression into specifically targeted tissue culture cells.

The present invention also encompasses transgenic animals whose cells contain the nucleic acid referenced above delivered via the chitosan-based compositions. These cells include germ or somatic cells. Transgenic animal models can be used for dissection of molecular carcinogenesis and disease, assessing potential chemical and physical carcinogens and tumor promoters, exploring model therapeutic avenues and livestock agricultural purposes.

The methods of use also include a method of treating human disease, which is another aspect of the present invention. The method of treatment includes the steps of administering the chitosan-based compositions as described herein so as to deliver a desired nucleic acid to a cell or tissue for the purposes of expression of the nucleic acid by the cell or tissue. Cell or tissue types of interest can include, but are not limited to: liver, muscle, lung, endothelium, joints, skin, bone, tumors and blood.

The methods of treatment or use include methods for delivering nucleic acid into a hepatocyte by contacting a hepatocyte with the above referenced chitosan-based compositions. The surface ligand used with the chitosan-based composition is one specific for recognition by hepatocyte receptors. In particular, the asialoorosomucoid protein is used as a cell surface ligand, apoE-3, or a derivative as a lipophilic peptide binding molecule and JTS-1 or a derivative as a lysis agent as described in U.S. patent application Ser. No. 08/584,043, titled "Lipophilic Peptides For Macromolecule Delivery", filed on Jan. 11, 1995, incorporated by reference herein in its entirety including any drawings or figures. Furthermore, these methods of use also include delivery of nucleic acids using a chitosan-based composition with apoE-3 and no surface or nuclear ligands. The term "hepatocyte" as used herein refers to cells of the liver.

An embodiment of the methods of treatment or use includes a method for delivering nucleic acid to muscle cells by contacting the muscle cell with one of the above referenced chitosan-based compositions. The surface ligand used is specific for receptors contained on the muscle cell. In particular, the surface ligand can be insulin-like growth factor-I. In addition, the lipophilic peptide binding molecule can be a apoE-3, or a derivative and the lysis agent can be JTS-1 or a derivative. Furthermore, these methods of treatment or use also include delivery of nucleic acids using a chitosan-based composition with apoE-3. The term "muscle cell" as used herein refers to cells associated with skeletal muscle, smooth muscle or cardiac muscle.

Another embodiment of the methods of treatment or use includes a method for delivering nucleic acid to bone-forming cells by contacting the bone-forming cell with the above referenced chitosan-based composition. The surface ligand used with the chitosan-based composition is specific for receptors associated with bone-forming cells. In particular, the surface ligands can include, but are not limited to, bone morphogenetic protein or cartilage induction factor. In addition, the lipophilic peptide binding molecule of a chitosan-based composition can be apoE-3, or a derivative, and the lysis agent JTS-1 or a derivative thereof. Furthermore, these methods of treatment or use also include delivery of nucleic acids using a chitosan-based composition with apoE-3. As used herein the term "bone-forming cell" refers to those cells which promote bone growth. Nonlimiting examples include osteoblasts, stromal cells, inducible osteoprogenitor cells, determined osteoprogenitor cells, chondrocytes, as well as other cells capable of aiding bone formation.

Another related embodiment of the methods of treatment or use includes a method for delivering nucleic acid to a cell using the above referenced chitosan-based compositions. The chitosan-based composition can use folate as a ligand. In addition, the chitosan-based compositions can use JTS-1 or a derivative as a lysis agent, and apoE-3, or a derivative thereof as a lipophilic peptide binding molecule. This method targets cells which contain folate receptors, including, but not limited to, hepatocytes.

Still another related embodiment of the methods of treatment or use includes a method for delivering nucleic acid to synoviocytes or macrophages using the above referenced chitosan-based compositions. The chitosan-based composition can use a ligand recognized by synoviocytes and/or macrophages. In addition, the chitosan-based composition can use JTS-1 or a derivative as a lysis agent, and apoE-3, or a derivative thereof as a lipophilic peptide binding molecule. Furthermore, this method of use also includes delivery of nucleic acids using a chitosan-based composition with apoE-3 and no surface or nuclear ligands. The term "synoviocytes" refers to cells associated with the joints or with the fluid space of the joints.

In addition to the above methods, the method of use also includes delivery using a nuclear ligand binding complex with the above-referenced chitosan-based compositions. Such nuclear carriers would help direct the chitosan-based composition to the nucleus of the cell. Furthermore, the above methods of use also include chitosan-based compositions with the lipophilic peptide binding molecule and the lysis agent, or any plurality of confirmation thereof.

III. Administration

Administration as used herein refers to the route of introduction of the chitosan-based composition into the body. Administration includes but is not limited to intravenous, intramuscular, systemic, subcutaneous, subdermal, topical, or oral methods of delivery. Administration can be directly to a target tissue or through systemic delivery.

In particular, the present invention can be used for administering nucleic acid for expression of specific nucleic acid sequence in cells. Routes of administration include intramuscular, aerosol, olfactory, oral, topical, systemic, ocular, intraperitoneal and/or intratracheal. A preferred method of administering chitosan-based compositions is by oral delivery. Another preferred method of administration is by direct injection into the cells or by systemic intravenous injection.

Transfer of genes directly has been very effective. Experiments show that administration by direct injection of DNA into joints and thyroid tissue results in expression of the gene in the area of injection. Injection of plasmids containing IL-1 into the spaces of the joints results in expression of the gene for prolonged periods of time. The injected DNA appears to persist in an unintegrated extrachromosomal state. This means of transfer is one of the preferred embodiments.

In addition, another means to administer the chitosan-based compositions of the present invention is by using a dry powder form for inhalation. Furthermore, administration may also be through an aerosol composition or liquid form into a nebulizer mist and thereby inhaled.

The special delivery route of any selected vector construct will depend on the particular use for the nucleic acid associated with the chitosan-based composition. In general, a specific delivery program for each chitosan-based composition used will focus on uptake with regard to the particular targeted tissue, followed by demonstration of efficacy. Uptake studies will include uptake assays to evaluate cellular uptake of the nucleic acid and expression of the specific nucleic acid of choice. Such assays will also determine the localization of the target nucleic acid after uptake, and establishing the requirements for maintenance of steady-state concentrations of expressed protein. Efficacy and cytotoxicity is then tested. Toxicity will not only include cell viability but also cell function.

Incorporated nucleic acid or oligonucleotide into chitosan-based compositions, as described herein, which undergo endocytosis increases the range of cell types that will take up foreign genes from the extracellular space.

The chosen method of delivery should result in cytoplasmic accumulation and optimal dosing. The dosage will depend upon the disease and the route of administration but should be between 0.1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Establishment of therapeutic levels of nucleic acid or oligonucleotide within the cell is dependent upon the rate of uptake and degradation. Decreasing the degree of degradation will prolong the intracellular half-life of the nucleic acid or oligonucleotide.

IV. Cell Transfection

One embodiment of the present invention includes cells transfected with nucleic acid associated with the chitosan-based compositions described above. Once the cells are transfected, the cells will express the protein, polypeptide or RNA encoded for by the nucleic acid. Cells include, but are not limited to, liver, muscle and skin. This description is not intended to be limiting in any manner.

The nucleic acid which contains the genetic material of interest is positionally and sequentially oriented within the host or vectors such that the nucleic acid can be transcribed into RNA and, when necessary, be translated into proteins or polypeptides in the transfected cells. A variety of proteins and polypeptides can be expressed by the sequence in the nucleic acid cassette in the transfected cells. These products may function as intracellular or extracellular structural elements, ligands, hormones, neurotransmitters, growth regulating factors, apolipoproteins, enzymes, serum proteins, receptors, carriers for small molecular weight compounds, drugs, immunomodulators, oncogenes, tumor suppressors, toxins, tumor antigens, antigens, antisense inhibitors, triple strand forming inhibitors, ribozymes, or as a ligand recognizing specific structural determinants on cellular structures for the purpose of modifying their activity.

Transfection can be done either by in vivo or ex vivo techniques. One skilled in the art will be familiar with such techniques for transfection. Transfection by ex vivo techniques includes co-transfecting the cells with nucleic acid containing a selectable marker. This selectable marker is used to select those cells which have become transfected. Selectable markers are well known to those who are skilled in the art.

For example, one approach to nucleic acid delivery for hepatic diseases is to remove hepatocytes from an affected individual, genetically alter them in vitro, and re-implant them into a receptive locus. The ex vivo approach includes the steps of harvesting hepatocytes, cultivating the hepatocytes, transducing or transfecting the hepatocytes, and introducing the transfected hepatocytes into the affected individual.

The hepatocytes may be obtained in a variety of ways. They may be taken from the individual who is to be later injected with the hepatocytes that have been transfected or they can be collected from other sources, transfected and then injected into the individual of interest.

Once the ex vivo hepatocyte is collected, it may be transfected by contacting the hepatocytes with media containing the chitosan-based composition and maintaining the cultured hepatocytes in the media for sufficient time and under conditions appropriate for uptake and transfection of the hepatocytes. The hepatocytes may then be introduced into an orthotopic location (the body of the liver or the portal vasculature) or heterotopic locations by injection of cell suspensions into tissues. One skilled in the art will recognize that the cell suspension may contain: salts, buffers or nutrients to maintain viability of the cells; proteins to ensure cell stability; and factors to promote angiogenesis and growth of the implanted cells.

In an alternative method, harvested hepatocytes may be grown ex vivo on a matrix consisting of plastics, fibers or gelatinous materials which may be surgically implanted in an orthotopic or heterotopic location after transduction. This matrix may be impregnated with factors to promote angiogenesis and growth of the implanted cells. Cells can then be re-implanted. The above are only examples and are nonlimiting.

V. Direct Delivery to the Liver

Chitosan-based compositions of the present invention can also be used in reversing or arresting the progression of disease involving the liver, such as liver cancer. One embodiment involves use of intravenous methods of administration to delivery nucleic acid encoding for a necessary molecule to treat disease in the liver. Chitosan-based compositions which express a necessary protein or RNA can be directly injected into the liver or blood supply so as to travel directly to the liver.

VI. Direct DNA Delivery to Muscle

The muscular dystrophies are a group of diseases that result in abnormal muscle development, due to many different reasons. These diseases can be treated by using the direct delivery of genes with the chitosan-based compositions of the present invention resulting in the production of normal gene product. Delivery to the muscle using the present invention is done to present genes that produce various antigens for vaccines against a multitude of infections of both viral, bacterial, and parasitic origin. The detrimental effects caused by aging can also be treated using the chitosan-based compositions described herein. Since the injection of the growth hormone protein promotes growth and proliferation of muscle tissue, the growth hormone gene can be delivered to muscle, resulting in both muscle growth and development, which is decreased during the later portions of the aging process. Genes expressing other growth related factors can be delivered, such as Insulin Like Growth Factor-1 (IGF-1). Furthermore, any number of different genes may be delivered by this method to the muscle tissue.

IGF-1 can be used to deliver DNA to muscle, since it undergoes uptake into cells by receptor-mediated endocytosis. This polypeptide is 70 amino acids in length and is a member of the growth promoting polypeptides structurally related to insulin. It is involved in the regulation of tissue growth and cellular differentiation affecting the proliferation and metabolic activities of a wide variety of cell types, since the polypeptide has receptors on many types of tissue. As a result, the chitosan-based compositions of the present invention can utilize IGF-1 as a ligand for tissue-specific nucleic acid delivery to muscle. The advantage of a IGF-1/nucleic acid delivery system is that the specificity and the efficiency of the delivery is greatly increased due to a great number of cells coming into contact with the ligand/composition with uptake through receptor-mediated endocytosis. Using the nucleic acid described above in the chitosan-based compositions of the present invention with the use of specific ligands for the delivery of nucleic acid to muscle cells provides treatment of diseases and abnormalities that affect muscle tissues.

VII. Direct DNA Delivery to Osteogenic Cells

There are many other problems that occur during the aging process, but one major problem is osteoporosis, which is the decrease in overall bone mass and strength. The direct delivery chitosan-based compositions of the present invention can be used to deliver genes to cells that promote bone growth. The osteoblasts are the main bone forming cell in the body, but there are other cells that are capable of aiding in bone formation. The stromal cells of the bone marrow are the source of stem cells for osteoblasts. The stromal cells differentiate into a population of cells known as Inducible Osteoprogenitor Cells (IOPC), which then under induction of growth factors, differentiate into Determined Osteoprogenitor Cells (DOPC). It is this population of cells that mature directly into bone producing cells. The IOPCs are also found in muscle and soft connective tissues. Another cell involved in the bone formation process is the cartilage-producing cell known as the chondrocyte.

A factor identified to be involved in stimulating the IOPCs to differentiate is known as Bone Morphogenetic Protein (BMP). This 19,000 MW protein was first identified from demineralized bone. Another similar factor is Cartilage Induction Factor (CIF), which also functions to stimulate IOPCs to differentiate thereby initiating cartilage formation, cartilage calcification, vascular invasion, resorption of calcified cartilage, and finally induction of new bone formation. Cartilage Induction Factor has been identified as being homologous to Transfecting Growth Factor $\beta$.

Since osteoblasts are involved in bone production, genes that enhance osteoblast activity can be delivered directly to these cells. Genes can also be delivered to the IOPCs and the chondrocytes, which can differentiate into osteoblasts, leading to bone formation. BMP and CIF are the ligands that can be used to deliver genes to these cells. Genes delivered to these cells promote bone formation or the proliferation of osteoblasts. The polypeptide, IGF-1 stimulates growth in hypophysectomized rats which could be due to specific uptake of the polypeptide by osteoblasts or by the interaction of the polypeptide with chondrocytes, which result in the formation of osteoblasts. Other specific bone cell and growth factors can be used through the interaction with various cells involved in bone formation to promote osteogenesis.

Nonlimiting examples of genes expressing the following growth factors which can be delivered to these cell types are Insulin, Insulin-Like Growth Factor-1, Insulin-Like Growth Factor-2, Epidermal Growth Factor, Transfecting Growth Factor-$\alpha$, Transfecting Growth Factor-$\beta$, Platelet Derived Growth Factor, Acidic Fibroblast Growth Factor, Basic Fibroblast Growth Factor, Bone Derived Growth Factors, Bone Morphogenetic Protein, Cartilage Induction Factor, Estradiol, and Growth Hormone. All of these factors have a positive effect on the proliferation of osteoblasts, the related stem cells, and chondrocytes. As a result, BMP or CIF can be used as conjugates to deliver genes that express these growth factors to the target cells by the intravenous injection of the nucleic acid/chitosan compositions of the present invention. Using the nucleic acid described above in the chitosan-based compositions of the present invention with the use of specific ligands for the delivery of nucleic acid to bone cells provides treatment of diseases and abnormalities that affect bone tissues.

VIII. Direct DNA Delivery to the Synoviocytes

The inflammatory attack on joints in animal models and human diseases may be mediated, in part, by secretion of cytokines such as IL-1 and IL-6 which stimulate the local inflammatory response. The inflammatory reaction may be modified by local secretion of soluble fragments of the receptors for these ligands. The complex between the ligand and the soluble receptor prevents the ligand from binding to the receptor is normally present on the surface of cells, thus preventing the stimulation of the inflammatory effect.

Therapy consists of the construction of a vector containing the soluble form of receptors for appropriate cytokines (for example, IL-1), together with promoters capable of inducing high level expression in structures of the joint and composition which enables efficient uptake of this vector. This composition is then used with the nucleic acid carried by the chitosan-based compositions of the present invention. This DNA is injected into affected joints where the secretion of an inhibitor for IL-1 such as a soluble IL-1 receptor or natural IL-I inhibitor modifies the local inflammatory response and resulting arthritis.

This method is useful in treating episodes of arthritis which characterize many "autoimmune" or "collagen vascular" diseases. This method can also prevent disabling injury of large joints by inflammatory arthritis.

In addition to the above, the present invention can also be used with the following method. Current therapy for severe arthritis involves the administration of pharmacological agents including steroids to depress the inflammatory response. Steroids can be administered systemically or locally by direct injection into the joint space.

Steroids normally function by binding to receptors within the cytoplasm of cells. Formation of the steroid-receptor complex changes the structure of the receptor so that it becomes capable of translocating to the nucleus and binding to specific sequences within the genome of the cell and altering the expression of specific genes. Genetic modifications of the steroid receptor can be made which enable this receptor to bind naturally occurring steroids with higher affinity, or bind non-natural, synthetic steroids, such as RU486. Other modifications can be made to create steroid receptor which is "constitutively active" meaning that it is capable of binding to DNA and regulating gene expression in the absence of steroid in the same way that the natural steroid receptor regulates gene expression after treatment with natural or synthetic steroids.

Of particular importance is the effect of glucocorticoid steroids such as cortisone, hydrocortisone, prednisone, or dexamethasone which are the most important drugs available for the treatment of arthritis. One approach to treating arthritis is to introduce a vector in which the nucleic acid cassette expresses a genetically modified steroid receptor into cells of the joint, e.g., a genetically modified steroid receptor which mimics the effect of glucocorticoids but does not require the presence of glucocorticoids for effect. This is termed the glucocortico-mimetic receptor. This is achieved by expression of a constitutively active steroid receptor within cells of the joint which contains the DNA binding domain of a glucocorticoid receptor. This induces the therapeutic effects of steroids without the systemic toxicity of these drugs.

Alternatively, steroid receptors which have a higher affinity for natural or synthetic glucocorticoids, such as RU486, can be introduced into the joint. These receptors exert an increased anti-inflammatory effect when stimulated by non-toxic concentrations of steroids or lower doses of pharmacologically administered steroids. Alternatively, constitution of a steroid receptor which is activated by a novel, normally-inert steroid enables the use of drugs which would affect only cells taking up this receptor. These strategies obtain a therapeutic effect from steroids on arthritis without the profound systemic complications associated with these drugs. Of particular importance is the ability to target these genes differentially to specific cell types (for example synovial cells versus lymphocytes) to affect the activity of these cells.

As described in U.S. Pat. No. 5,364,791 to Vegeto, et al., entitled "Progesterone Receptor Having C Terminal Hormone Binding Domain Truncations," and U.S. application, Ser. No. 07/939,246, entitled "Mutated Steroid Hormone Receptors, Methods for Their Use and Molecular Switch for Gene Therapy," Vegeto, et al., filed Sep. 2, 1992, both hereby incorporated by reference (including drawings), genetically modified receptors, such as the glucocortico-mimetic receptor, can be used to create novel steroid receptors including those with glucocortico-mimetic activity. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either up-regulate or down-regulate transcription.

The preferred receptor of the present invention is modification of the glucocorticoid receptor, i.e., the glucocorticoid-mimetic receptor. These receptors can be modified to allow them to bind various ligands whose structure differs from naturally occurring ligands, e.g., RU486. For example, small C-terminal alterations in amino acid sequence, including truncation, result in altered affinity and altered function of the ligand. By screening receptor mutants, receptors can be customized to respond to ligands which do not activate the host cells own receptors.

A person having ordinary skill in the art will recognize, however, that various mutations, for example, a shorter deletion of carboxy terminal amino acids, will be necessary to create useful mutants of certain steroid hormone receptor proteins. Steroid hormone receptors which may be mutated are any of those receptors which comprise the steroid hormone receptor super family, such as receptors including the estrogen, progesterone, glucocorticoid-α, glucocorticoid-β, mineral corticoid, androgen, thyroid hormone, retinoic acid, and Vitamin B3 receptors. Furthermore, DNA encoding for other mutated steroids such as those which are capable of only transrepression or of only transactivation are also within the scope of the above embodiment. Such steroids could be capable of responding to RU486 in order to activate transrepression.

In addition to the above, the present invention can also be used with the following method. Drugs which inhibit the enzyme prostaglandin synthase are important agents in the treatment of arthritis. This is due, in part, to the important role of certain prostaglandin in stimulating the local immune response. Salicylates are widely used drugs but can be administered in limited doses which are often inadequate for severe forms of arthritis.

Gene transfer using the present invention is used to inhibit the action of prostaglandin synthase specifically in affected joints by the expression of an antisense RNA for prostaglandin synthase. The complex formed between the antisense RNA and mRNA for prostaglandin synthase interferes with the proper processing and translation of this mRNA and lowers the levels of this enzyme in treated cells. Alternatively RNA molecules are used for forming a triple helix in regulatory regions of genes expressing enzymes required for prostaglandin synthesis. Alternatively, RNA molecules are identified which bind the active site of enzymes required for prostaglandin synthesis and inhibit this activity.

Alternatively, genes encoding enzymes which alter prostaglandin metabolism can be transferred into the joint. These have an important anti-inflammatory effect by altering the chemical composition or concentration of inflammatory prostaglandin.

Likewise, the present invention is useful for enhancing repair and regeneration of the joints. The regenerative capacity of the joint is limited by the fact that chondrocytes are not capable of remodeling and repairing cartilaginous tissues such as tendons and cartilage. Further, collagen which is produced in response to injury is of a different type lacking the tensile strength of normal collagen. Further, the injury collagen is not remodeled effectively by available collagenase. In addition, inappropriate expression of certain metalloproteinases is a component in the destruction of the joint.

Gene transfer using promoters specific to chondrocytes (i.e., collagen promoters) is used to express different collagens or appropriate collagenase for the purpose of improving the restoration of function in the joints and prevent scar formation.

Gene transfer for these purposes is affected by direct introduction of nucleic acid into the joint space where it comes into contact with chondrocytes and synovial cells. Further, the genes permeate into the environment of the joint where they are taken up by fibroblasts, myoblasts, and other constituents of periarticular tissue.

IX. Direct Delivery to the Lungs

Chitosan-based compositions of the present invention can also be used in reversing or arresting the progression of disease involving the lungs, such as lung cancer. One embodiment involves use of intravenous methods of administration to delivery nucleic acid encoding for a necessary molecule to treat disease in the lung. Chitosan-based compositions which express a necessary protein or RNA can be directly injected into the lungs or blood supply so as to travel directly to the lungs. Furthermore, the use of an aerosol or a liquid in a nebulizer mist can also be used to administer the desired nucleic acid to the lungs. Finally, a dry powder form can be used to treat disease in the lung. The dry powder form is delivered by inhalation. These treatments can be used to control or suppress lung cancer or other lung diseases by expression of a particular protein encoded by the nucleic acid which is chosen to be delivered.

Additional organs, tissues, cavities, cell or cells, spaces for the administration of the molecules mentioned herein may be found in "Nucleic Acid Transporters for Delivery of Nucleic Acids into a Cell"; Smith et al., U.S. patent application Ser. No. 08/484,777, filed Dec. 18, 1995, incorporated herein by reference in its entirety including any drawings.

EXAMPLES

The following examples show methods of depolymerizing chitosan and characterizing chitosan and chitosan oligomers, methods of complexing chitosan and characterizing chitosan-based compositions, methods of preparation of low weight molecular chitosans, methods of sodium nitrite treatment of chitosans, the relation of the size of chitosan-based compositions to the molecular weight of chitosans used in the composition, modifications of chitosan-based compositions, the net charge on chitosan-based compositions, in vivo and in vitro studies of chitosan-based compositions, and studies of the oral administration of chitosan-based compositions. The examples are solely for illustrative purposes and are not meant to be limiting on the scope of the invention. The invention is limited by the scope of the claims.

Materials Used

SEACURE 143 (78.9% deacetylated), SEACURE 243 (80.1% deacetylated), and SEACURE 340 (82.3% deacetylated) were obtained from PRONOVA BIOPOLYMER (Raymond, Wash.). The viscosities of 1% chitosan solutions (143, 243, and 340) in 1% acetic acid were given as 14 cP, 90 cP, and 680 cP, respectively. These viscosities corresponded to average molecular weights of approximately 110 kDa, 230 kDa, and 540 kDa, respectively. SEACURE L210 (Poly-D-glucosamine hydrolactate) was also obtained from PRONOVA BIOPOLYMER (>80% deacetylated; 78 cP) for analysis. Glucosamine hydrochloride was obtained from Fluka BioChemika (AG CH-9470 Buchs). Sodium nitrite A.C.S. was from Fisher Scientific (Fair Lawn, N.J.). Lactose monohydrate powder U.S.P. was from Penta Manufacturing (Livingston, N.J.). A endosomolytic (lytic) peptide (LP) was synthesized and purified. DNA plasmids, containing a CMV promoter and either chloramphenicol acetyltransferase (CMV-CAT) or B-galactosidase reporter gene (CMV-B-gal), were prepared and purified. A chemiluminescence detection system for B-galactosidase (Galacto-Light™) was from Tropix, Inc. (Bedford, Mass.). A CAT ELISA kit was obtained from Boehringer Mannheim (GmbH, Germany).

Example 1

De-Polymerization of Chitosan

Chitosan (SEACURE 143) was de-polymerized according to a modified method described by Peniston et al., U.S. Pat. No. 3,922,260; Nov. 25, 1975 incorporated by reference in its entirety including any drawings or figures. Briefly, five-2 g (0.0124 moles) solutions of SEACURE 143 in 100 ml of normal (6%) acetic acid were treated at 25° C. with five corresponding solutions of $NaNO_2$ in 6% acetic acid. The five corresponding $NaNO_2$ solutions contained $1.24 \times 10^{-4}$ moles $NaNO_2$, $2.48 \times 10^{-4}$ moles $NaNO_2$, $4.96 \times 10^{-4}$ moles $NaNO_2$, $7.44 \times 10^{-4}$ moles $NaNO_2$, and $1.24 \times 10^{-3}$ moles $NaNO_2$, respectively. The five reactions corresponded to 1%, 2%, 4%, 6%, and 10% of the theoretical amount of $NaNO_2$ needed for complete deamination of chitosan. The $NaNO_2$ was added over a 30 minute period using vigorous magnetic stirring. The reactions were allowed to continue for a total of 3 hours at which time the five solutions were neutralized with dilute sodium hydroxide to pH 7.4. The precipitated products were centrifuged for 10 minutes at 4000 rpm, washed 2 times with water, centrifuged two times as above, washed in ethanol and centrifuged twice, again as above, washed in ether and centrifuged again, as above, then vacuum dried at 25° C. for 2 days. The weight yield (from 2 g SEACURE 143 original) was 70%, 80%, 75%, 61%, and 32%, respectively.

Example 2

Characterization of Chitosan and Chitosan Oligomers

The molecular weights of SEACURE 143 and de-polymerized SEACURE 143 products were determined using a Beckman Ultraspherogel SEC2000 Column using a mobile phase of 0.1M HOAc-NaOAc buffer (pH 5.5) with 0.05 M NaCl. A flow rate of 1 ml/min was employed with both UV detection at 280 nm and refractive index. Polyethylene glycol (PEG) was used as the molecular weight standard. The percent (%) Nitrogen was determined by Atlantic Microlab, Inc. (Norcross, Ga.) using combustion analysis. Viscosities of chitosan and chitosan oligomers at 4 ug/ml in 0.2% acetic acid were determined using a Brookfield Model DV-III Programmable Rheometer (Stoughton, Mass.). A Beckman DU640 Spectrophotometer was used to determine the absorbance of 1 ug/ml solutions of chitosan and chitosan oligomers in 0.2% acetic acid diluted with water.

The amine content of chitosan and chitosan oligomers was determined using a modified ninhydrin assay as described by Curotto et al., *Analy. Biochem.*, 211 240–241 (1993). Briefly, chitosan and chitosan oligomers were vacuum dried overnight and dissolved in 2% acetic acid at a concentration of 1 mg/ml. Then to different volumes of 0.5 ml of 4 M acetic acid/acetate buffer (pH 5.5) was added the sample (i.e., 100–500 ml). Each solution was standardized to a volume of 1 ml with water. Then, 2 ml ninhydrin reagent (J. L. Bailey. In: *Techniques in Protein Chemistry*. (1967) 348–349. Elsevier, Amsterdam, The Netherlands) was added to the samples which were vigorously mixed using vortex mixing. The samples were incubated at 100° C. for 20 minutes and cooled on ice to 0° C. The absorbance of each sample was measured at 570 nm against a ninhydrin reagent blank. All samples were completed in triplicate and compared to a glucosamine standard (100% amine content).

Example 3

Complexation of Chitosan and Chitosan Oligomers With DNA

Chitosan or chitosan oligomers were dissolved to 4 mg/ml in dilute acetic acid (either 0.2% or 1%) and sterile filtered (0.2 mm). The resulting filtered higher molecular weight chitosans (SEACURE 243 and SEACURE 340) were dissolved in 1% acetic acid and sonicated with heat to promote dissolution. The lower filtered molecular weight chitosan and chitosan oligomers (8 kDa, 13 kDa, 22 kDa, 41 kDa, 70 kDa, and SEACURE 143) were dissolved in 0.2% acetic acid without sonication.

Chitosan or chitosan oligomers (4 mg/ml in either 0.2% or 1% acetic acid) were added to 100–400 μg DNA in water or lactose, so that the final charge ratio (−/+) of the compositions ranged from 1:0.8 (−/+) to 1:12 (−/+) in per 1 ml of carrier solution for compositions made in lactose. The final lactose concentration was 10% (isotonic). An endosomolytic (lytic) peptide was added by electrostatic interaction to selected compositions.

Example 4

Characterization of DNA:Chitosan and DNA:Chitosan Oligomer Compositions

The unimodal size of the compositions was measured using a Model N4MD Particle Sizer. For all samples, measurements were made at 90° for 120 seconds using a viscosity setting of 1.005 cP and refractive index setting of 1.333. To characterize the size and morphology of compositions by transmission electron microscopy (TEM), a JEOL Electron Microscope was utilized. Carbon coated 200 mesh copper specimen grids were glow-discharged for 1.5 minutes. One drop of complex complexation was deposited on the grid and allowed to stand for 1.5 minutes. Excess liquid was removed using filter paper. Next, 1 drop of 1% uranyl acetate solution (0.2 µm filtered) was deposited on the grid and allowed to stain the sample for 10 minutes prior to examination of the samples under the electron microscope. Zeta potential values were measured using a Coulter DELSA 440 (Amherst, Mass.).

In initial studies designed to show that chitosan could complex and condense DNA into a compact particle, a correlation was found between the molecular weight of the commercially available chitosans and the resulting particle size of the complex formed with DNA, irrespective of the ratio of DNA to chitosan. The particle size of the resulting complex increased proportionally to the molecular weight of the chitosan substance used (i.e., SEACURE 340>SEACURE 243>SEACURE 143). This effect could be due to solubility differences with the chitosan substances since solubility of chitosan is known to increase as molecular weight of the substance decreases (i.e., SEACURE 143>SEACURE 243>SEACURE 340). Further evidence to support the solubility effect was reported by Shiraishi et al., *J. Contr. Rel.*, 25 217–225 (1993); and T. Imai et al., *Int. J. Pharm.*, 67 11–20(1991) both incorporated by reference in their entirety including drawings and figures. Shiraishi et al., report that lower molecular weight chitosans interact with indomethacin through hydrophobic and ionic interactions and that the extent of interaction depends on the molecular weight of chitosan. However, the intermolecular and intramolecular interactions, which promote complexation, increased with increasing molecular weight of chitosan. Nevertheless, the authors demonstrated that the release of indomethacin from the complex with chitosan was dominated by penetration of water into the substance matrix. Whereas chitosans of lower molecular weight (having increased solubility), allowed more water penetration. Higher molecular weight chitosans (having decreased solubility), caused substantial dehydration of the composition. Analogous to this effect, DNA compositions made with higher molecular weight chitosan should theoretically have reduced solubility resulting in aggregation and/or larger particle size. Such results were observed by us.

Example 5

Preparation of Low Molecular Weight Chitosans

As a result of the effect observed with chitosans having different molecular weights in Example 4, we hypothesized that the preparation of even smaller chitosan-based compositions would require the use of even lower molecular weight chitosans which were not commercially available. Thus, we modified a process for sodium nitrite de-polymerization of chitosan as described by Peniston et al. U.S. Pat. No. 3,922,260 to produce such lower molecular weight chitosans.

Peniston et al., describe the deaminative cleavage of chitosan into reduced chain-length oligomers to reduce viscosity, increase solubility, or to generally alter the molecular characteristics of chitosan as a polyelectrolyte. In Peninston et al's. reaction, sodium nitrite is converted to the reactive species nitrous acid by treatment with a strong acid (i.e., 6% acetic acid). Nitrous acid reacts only with the glucosamine moieties on chitosan, not the N-acetylglucosamine units. The reaction is believed to form a highly unstable diazonium salt which leads to the evolution of nitrogen and the replacement of the original amino group with a hydroxyl group resulting in a 2,5-anhydro-D-mannose residue at the new reducing end. In some instances, the reduced end results in the formation of olefins. In general, the release of nitrogen is stoichiometric with the loss of the amino group so that quantification of the released nitrogen gas can be directly correlated to the percentage (%) of deamination that has occurred.

Peniston et al., note that the nitrous acid reaction with chitosan results in an unexpected marked decrease in viscosity (and thus, molecular weight) with only small changes in percent (%) amine content. Thus, we anticipated that the nitrous acid induced deamination of higher molecular weight chitosan may be useful for reducing its molecular weight without causing a large reduction in the amine content which is needed for complexing and condensing DNA.

We also considered utilizing an alternative de-polymerization process for chitosan involving the treatment of chitosan with concentrated HCl at elevated temperatures (A. D. Domard and N. Cartier. *Glucosamine Oligomers: 1. Preparation and Characterization. Int. J. Biol. Macromol.*, 11 (1989) 297–302). This chemical method appeared suitable for making very pure chitosan oligomers, however separation of the product is difficult and costly and typically results in oligomers with very low degrees of polymerization (i.e., DP=20–37).

Example 6

Results of Sodium Nitrite Treatment of Chitosans

The results of the sodium nitrite treatment of chitosan (SEACURE 143) are shown in Table 2.

TABLE 2

Summary of Chitosan and De-polymerized Chitosan Oligomers

| No. | Starting Chitosan | % NaNO$_2$ treated | Mw (kDa)[a] | % Nitrogen (w/w)[b] | Viscosity (cP)[c] | Absorbance[d] at 280 nm | Normalized[e] % NH$_2$ |
|---|---|---|---|---|---|---|---|
| 1 | Seacure 143 | 0 | 90 | 7.98 ± 0.05 | 4.19 ± 0.07 | 0.06 | 78.9 |
| 2 | Seacure 143 | 1 | 70 | 7.96 ± 0.06 | 1.90 ± 0.01 | 0.10 | 77.2 |
| 3 | Seacure 143 | 2 | 41 | 7.70 ± 0.01 | 1.42 ± 0.01 | 0.17 | 73.4 |
| 4 | Seacure 143 | 4 | 22 | 7.44 ± 0.03 | 1.17 ± 0.01 | 0.35 | 70.9 |
| 5 | Seacure 143 | 6 | 13 | 7.48 ± 0.03 | 1.08 ± 0.01 | 0.53 | 70.9 |
| 6 | Seacure 143 | 10 | 8 | 7.34 ± 0.06 | 1.02 ± 0.01 | 0.84 | 69.0 |

[a]Beckman Ultraspherogel SEC2000; Mobile Phase: 0.1M HOAc-NaOAc pH 6; Flow rate of 1 mL/min; UV detection at 280 nm wavelength.
[b]Nitrogen content determined by Atlantic Microlab. Inc. Noecross, Georgia TABLE 2-continued Summary of Chitosan and De-polymerized Chitosan Oligomers

| No. | Starting Chitosan | % NaNO$_2$ treated | Mw (kDa)[a] | % Nitrogen (w/w)[b] | Viscosity (cP)[c] | Absorbance[d] at 280 nm | Normalized[e] % NH$_2$ |
|---|---|---|---|---|---|---|---|

[c]Viscosity determined using a Brookfield Model DV-III Programmable Rheometer using samples at 4 mg/mL in 0.2% acetic acid.
[d]Absorbance of samples at 1 mg/mL in diluted 0.2 acetic acid determined using a Beckman DU640 Spectrophotomer.
[e]Determined by modified ninhydrin assay described by E. Curotto et al. Experimental values obtained in the assay were normalized to the specifications of the supplier for Seacure 143 (#1 above).

A decrease in the molecular weight of chitosan was observed with increasing treatment by sodium nitrite. The decrease in molecular weight, as determined by gel permeation chromatography, also correlated well with the reduction in viscosity of 4 mg/ml solutions. The substantial loss in molecular weight of chitosan was not associated with a corresponding loss of nitrogen or amine content. However, we obtained a deacetylation value of 56% using the modified ninhydrin assay for SEACURE 143. This value was lower than the deacetylation value for SEACURE 143 specified by the manufacturer (78.9%). It is unclear why we obtained this lower value, since complexation and gel retardation assays confirmed the percentage amine content of the SEACURE 143 obtained from the manufacturer as 78.9%.

However, the modified ninhydrin assay did confirm that the amine percentage of chitosans treated with sodium nitrite did not change appreciably, although the molecular weight was markedly reduced.

Support for the creation of olefin byproducts as a result of sodium nitrite treatment of chitosan was supported by the observation of a positive absorbance peak at 280 nm in the treated chitosan compounds. The absorbance values were directly proportional to the amount of sodium nitrite treatment. Although the presence of the olefin side product reduced the "purity" of the chitosan oligomers, the ability to accurately quantify the concentration of chitosan oligomer in solution proved to be very useful in characterizing solutions and formed compositions.

Example 7

Relation of Chitosan Molecular Weight to Complex Size

Figure 2:
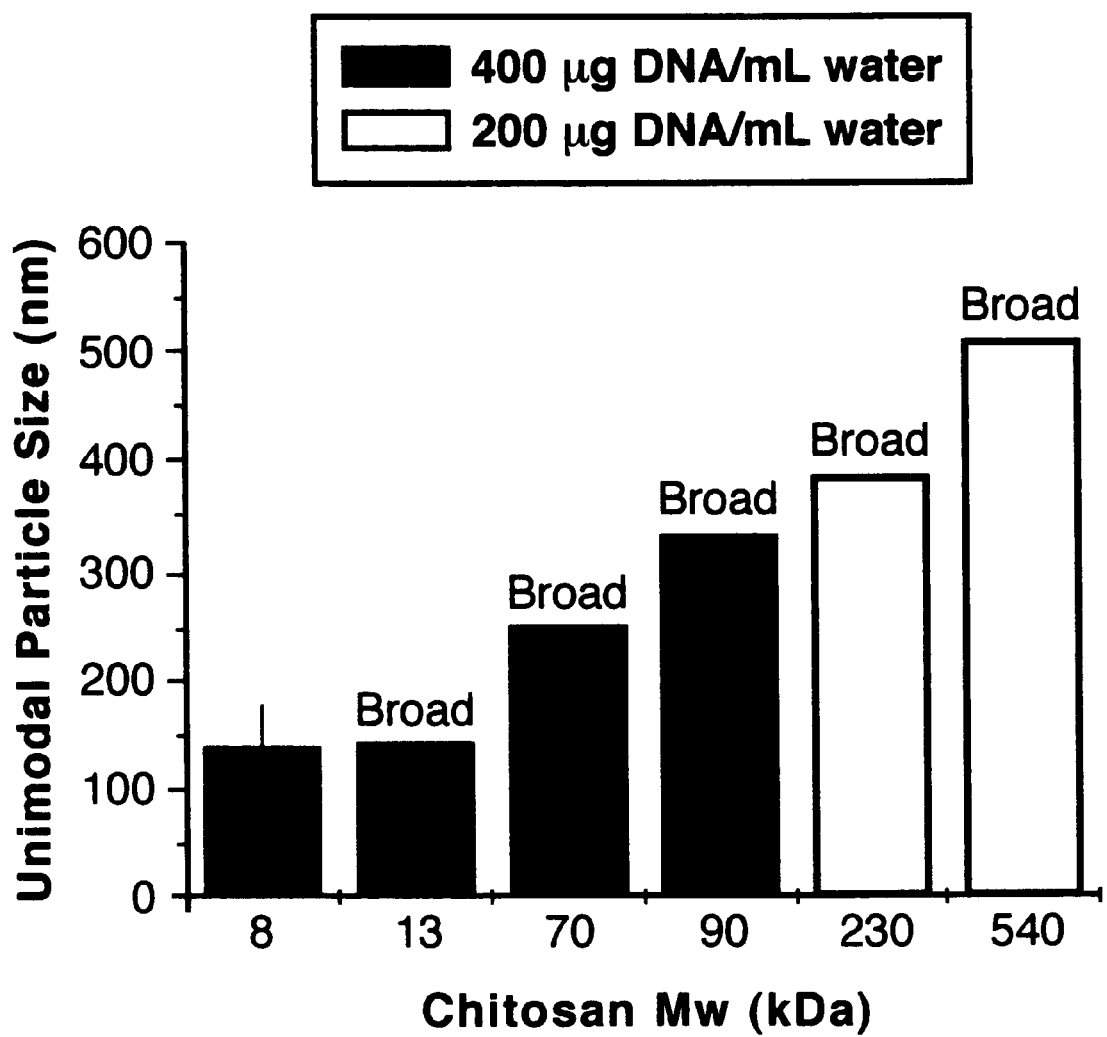
FIG. 2 is a graph of the effect of chitosan and chitosan oligomer molecular weight on the resulting particle size of chitosan-based compositions containing DNA plasmids. The charge ratio of all DNA:Chitosan compositions was 1:4 (−/+). The final pH of these complexations ranged from pH 5 (for high molecular weight chitosan-based compositions to pH 7.4 (for lower molecular weight chitosan oligomer compositions).

After performing the de-polymerization reactions on chitosan (SEACURE 143), we examined the effect of different molecular weight chitosans on the resulting particle size of compositions formed between DNA and these chitosans. The results are shown in FIG. 2.

For unimodal particle size of DNA:Chitosan compositions (1:4 −/+) in water there was a positive correlation between low molecular weight chitosan and the ability to form compositions of small size in water (irrespective of DNA concentration). These results support the fact that increased solubility of chitosan oligomers led directly to smaller and more stable compositions with increased colloidal solubility. The final pH of these DNA:Chitosan compositions ranged from pH 5 (for high molecular weight chitosan-based compositions to pH 7.4 (for lower molecular weight chitosan compositions).

Figure 3:
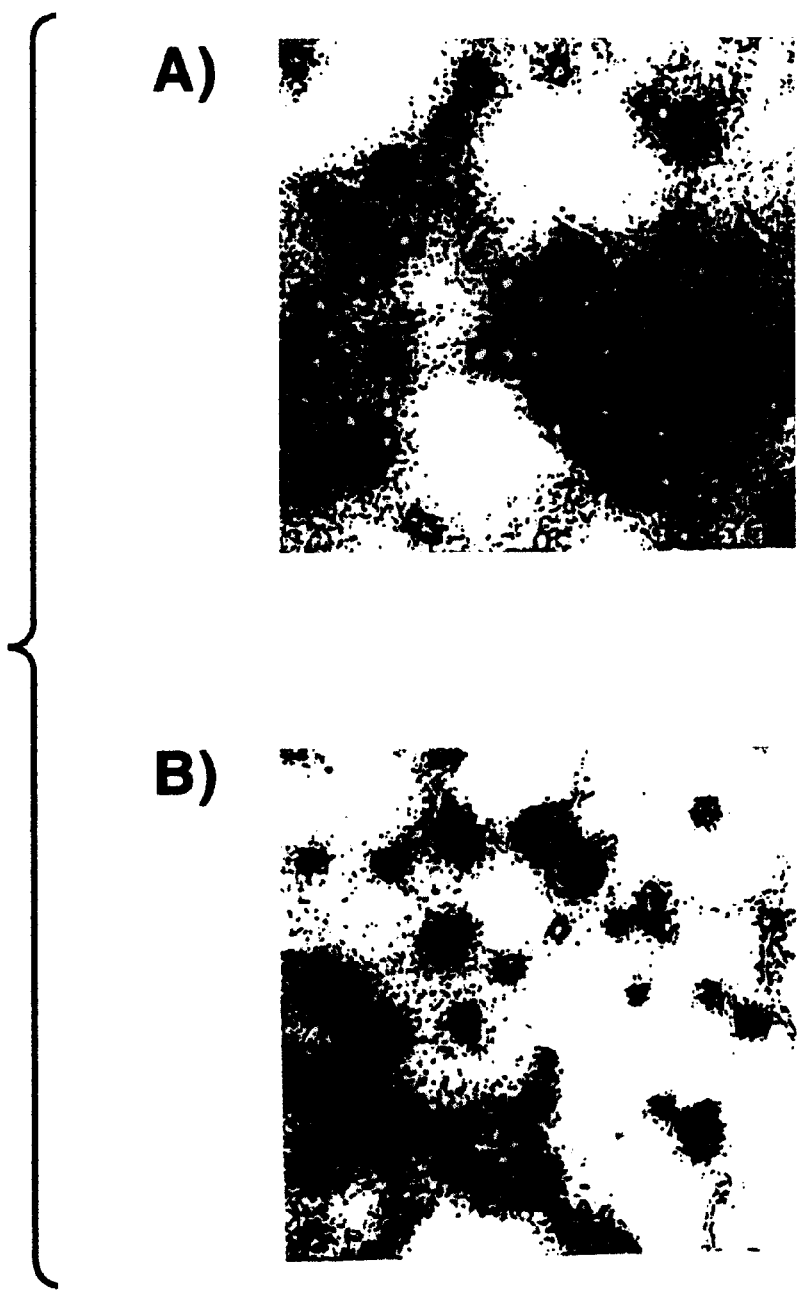
FIGS. 3A and 3B are a transmission electron micrography (TEM) of two complex compositions made with chitosan oligomer (8 kDa). A) DNA:Chitosan:Lytic Peptide (1:6:1 −/+/−) made in water with a DNA concentration of 50 μg/ml. The particle size of the composition as measured by light scattering was 64±16 nm. B) DNA:Chitosan (1:12 −/+) made in water with a DNA concentration of 50 μg/ml. The particle size of the complex as measured by light scattering was 66±24 nm.

Transmission electron micrographs (TEM) of two DNA-:Chitosan compositions made with a chitosan oligomer of 8 kDa in molecular weight are shown in FIG. 3 (A&B). Two shapes can be observed: toroidal or circular particles (toroids) and compact rod-like particles (rods). Similar toroids and rods have been reported to coexist in the literature (Y. Y. Vengerov and T. E. Semenov *Electron Microsc. Rev.*, 5; 193–20 (1992). Vengerov et al. have also shown that DNA can be condensed by a tri-valine peptide (TVP; H-Val-Val-Val-NH-NH-Dns where Dns is 5-dimethyl-aminoaphtyl-sulfonic acid) into compact rod-like structures where DNA molecules are interwound and lay side by side. This effect becomes more pronounced when the concentration of the TVP peptide is increased. The thick rods, described as 'comma-shaped' globules, are similar in shape to those in our studies.

Example 8

Effect of Analogues Added to Chitosan Complex

Figure 4:
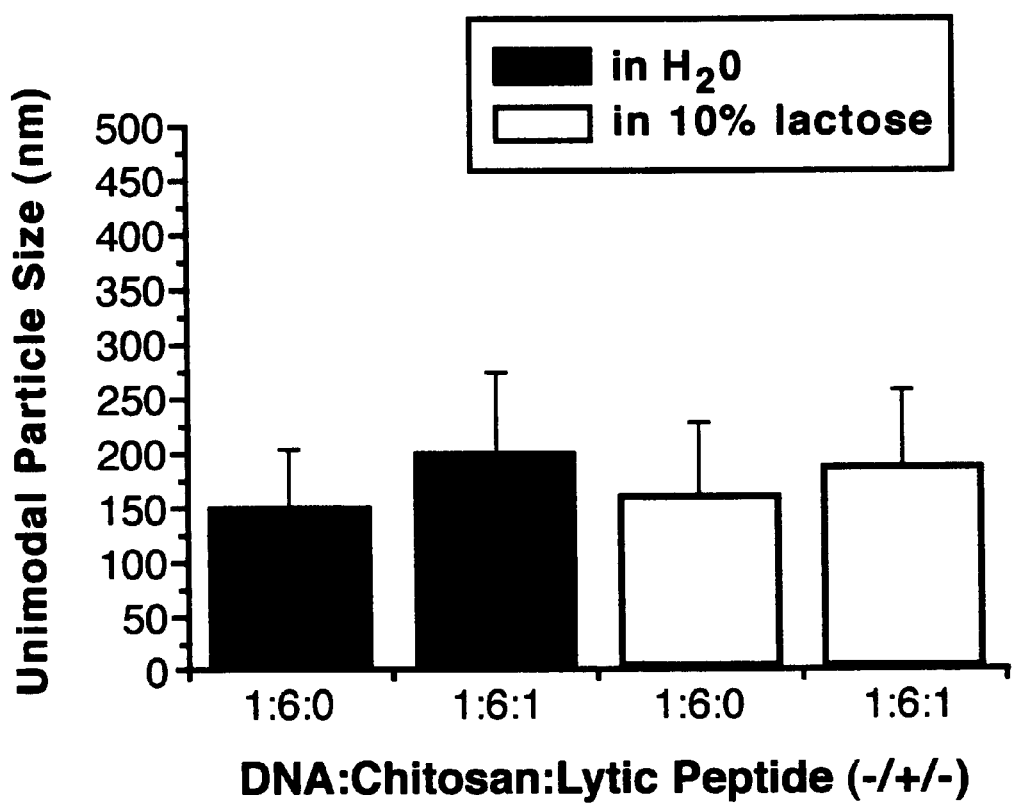
FIG. 4 is a graph of the effect of adding a negatively charged lytic peptide to preformed DNA:Chitosan (8 kDa) compositions and the effect of making such compositions in isotonic 10% lactose solutions with a DNA concentration of 100 μg/ml.

The effect of adding a negatively charged endosomolytic peptide to preformed DNA:Chitosan (8 kDa) compositions and the effect of their preparation in isotonic 10% lactose solutions is shown in FIG. 4.

The presence of the lytic peptide caused a small increase in the size of the composition, however, the presence of 10% lactose had no effect. Thus, chitosan compositions prepared in isotonic solutions can be used for intravenous administration, or lyophilized in the presence of lactose as a cryoprotectant for storage and subsequent use after rehydration.

Example 9

Effect of Cryoprotectant on Chitosan Complex

Figure 5:
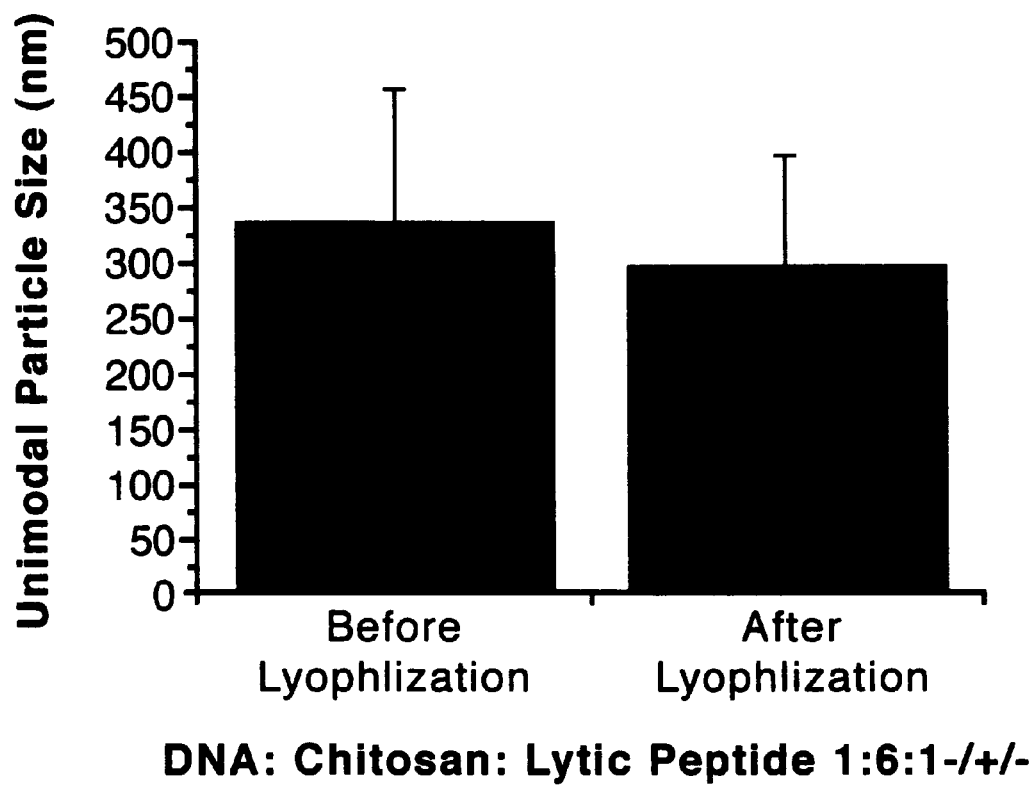
FIG. 5 graphs the effect of lyophilization and rehydration on the particle size of DNA:Chitosan (90 kDa):Lytic Peptide (1:6:1 −/+/−) compositions. The composition was mixed in 10% lactose with a DNA concentration of 100 μg/ml, lyophilized, and rehydrated with water to a final DNA concentration of 100 μg/ml.

The effect of lyophilization and rehydration on the particle size of DNA:Chitosan (90 kDa):Lytic Peptide(1:6:1 −/+/−) compositions is shown in FIG. 5. The colloidal properties of the composition are maintained during lyophilization and the size of the composition remains unaffected by the treatment.

The effect of adding a negatively charged lytic peptide to preformed DNA:Chitosan (8 kDa) compositions and the effect of making such compositions in isotonic 10% lactose solutions is graphically shown in FIG. 4. Under similar conditions compositions made with lower molecular weight chitosan (8 kDa) are approximately 2-fold smaller or more condensed than compositions made using higher molecular weight chitosan (90 kDa).

The effect of lyophilization and rehydration on the particle size of DNA:Chitosan(90 kDa):Lytic Peptide compositions with a charge ratio of (1:6:1 −/+/−) is shown in FIG. 5. Lyophilization and subsequent rehydration did not significantly effect the size of the compositions.

Example 10

Effect of Net Charge on Chitosan Complex

To reconfirm these results we produced DNA:Chitosan compositions of assorted charge ratios, by varying the amount of negatively charged lytic peptide in the composition.

Figure 6A:
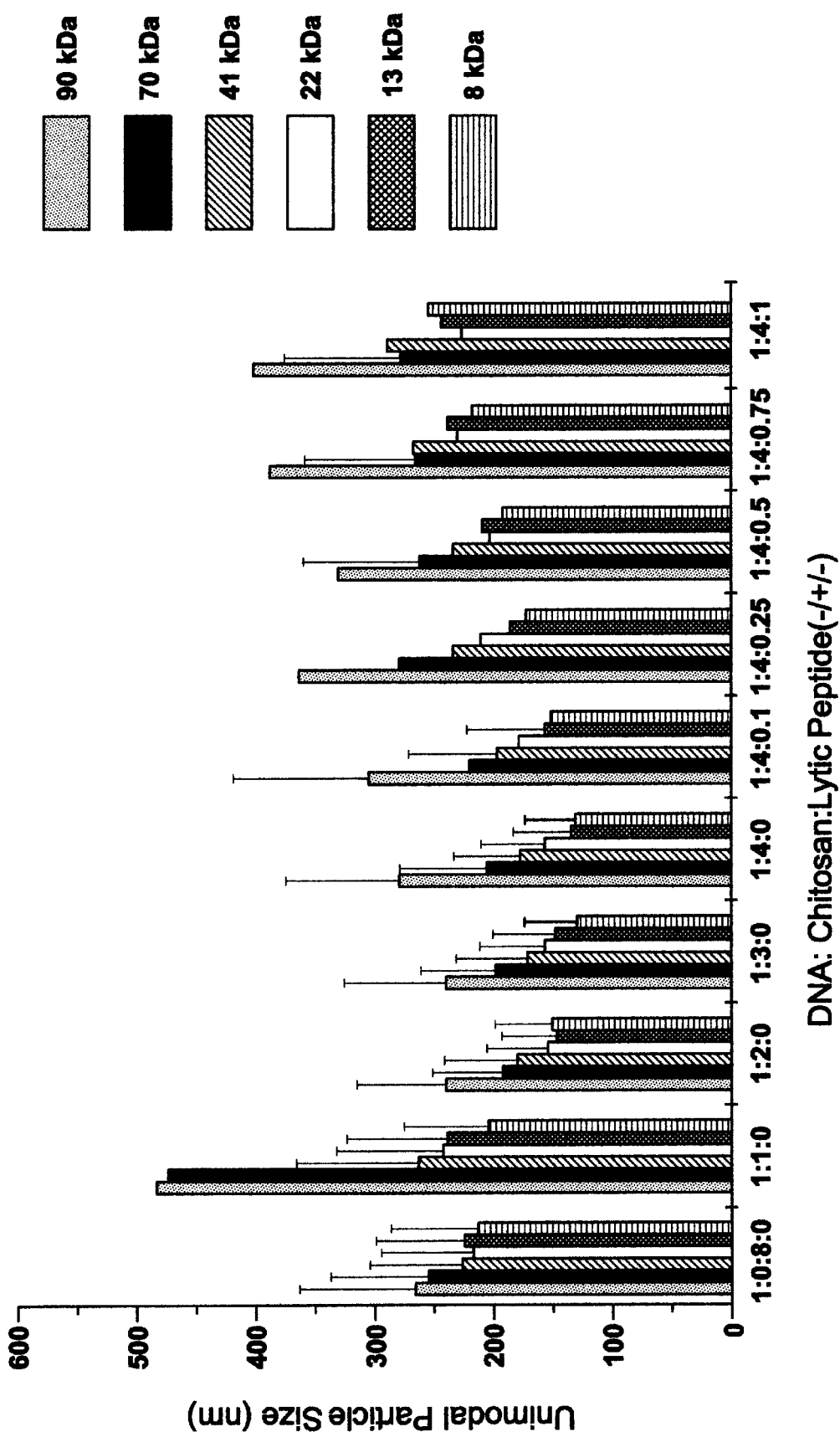
FIGS. 6A, 6B and 6C graph the effect on composition of a chitosan-based compound with and without the inclusion of a lytic peptide. All compositions were made in water with a DNA concentration of 200 μg/ml. Panel (A) shows the overall results of particle size, Panel (B) shows the effect of chitosan molecular weight and complex charge ratio on the size of the compositions, and Panel (C) shows the effect of chitosan molecular weight, complex charge ratio, and the inclusion of various amount of lytic peptide on the size of the compositions.
Figure 6B:
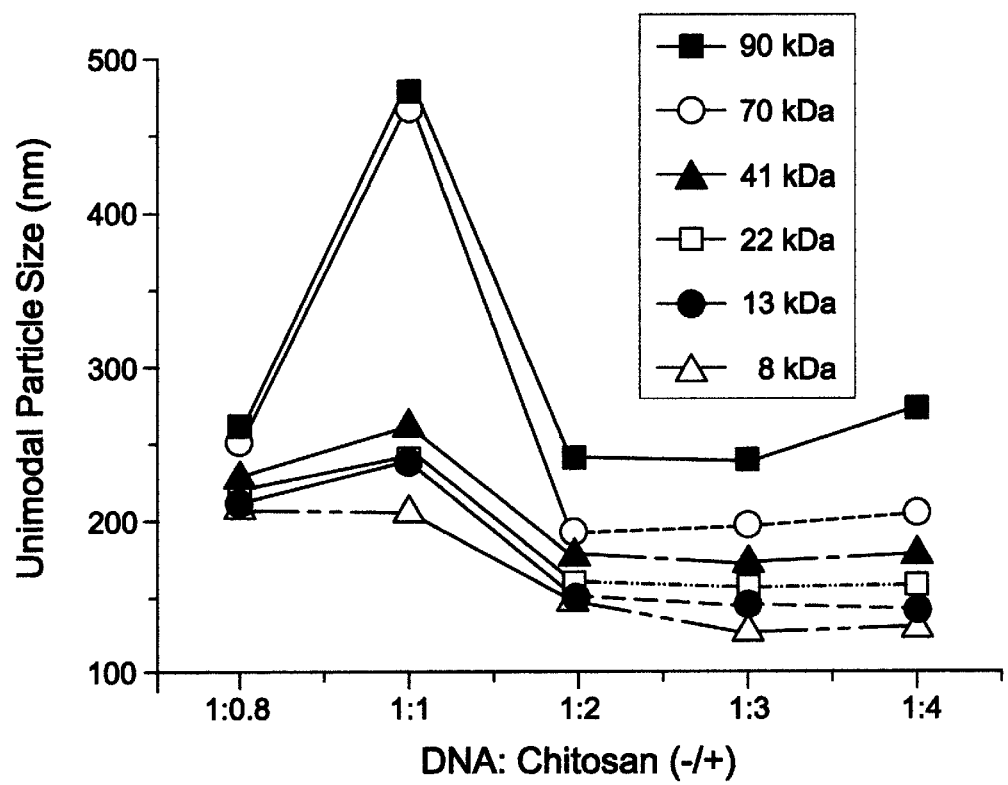
Figure 6C:
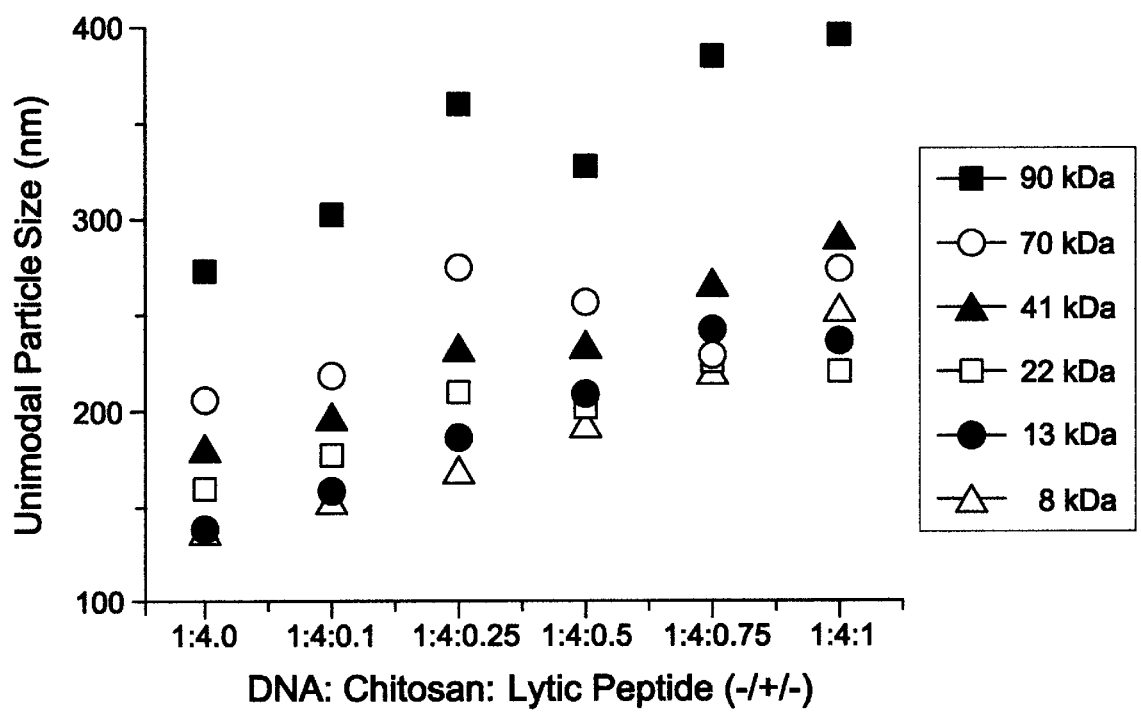

The results are depicted in FIG. 6A. Composition size without and with lytic peptide are shown in FIG. 6 (b & c respectively).

In general, with increasing positive charge the particle size decreased in compositions (without the lytic peptide) until a charge ratio of 1:2 (−/+) was achieved. Thereafter, increasing the positive charge had little or only a slight effect on particle size. The largest increase in particle size was observed in compositions made with chitosan-based compounds greater than 41 kDa in weight; most likely due to their decreased solubility.

Addition of negatively charged lytic peptide to the compositions resulted in an approximately linear increase in their size regardless of the weight of the chitosan used in the composition. The observed increase in size may be due to charge competition or to a change in the solubility of the composition colloid.

Figure 7:
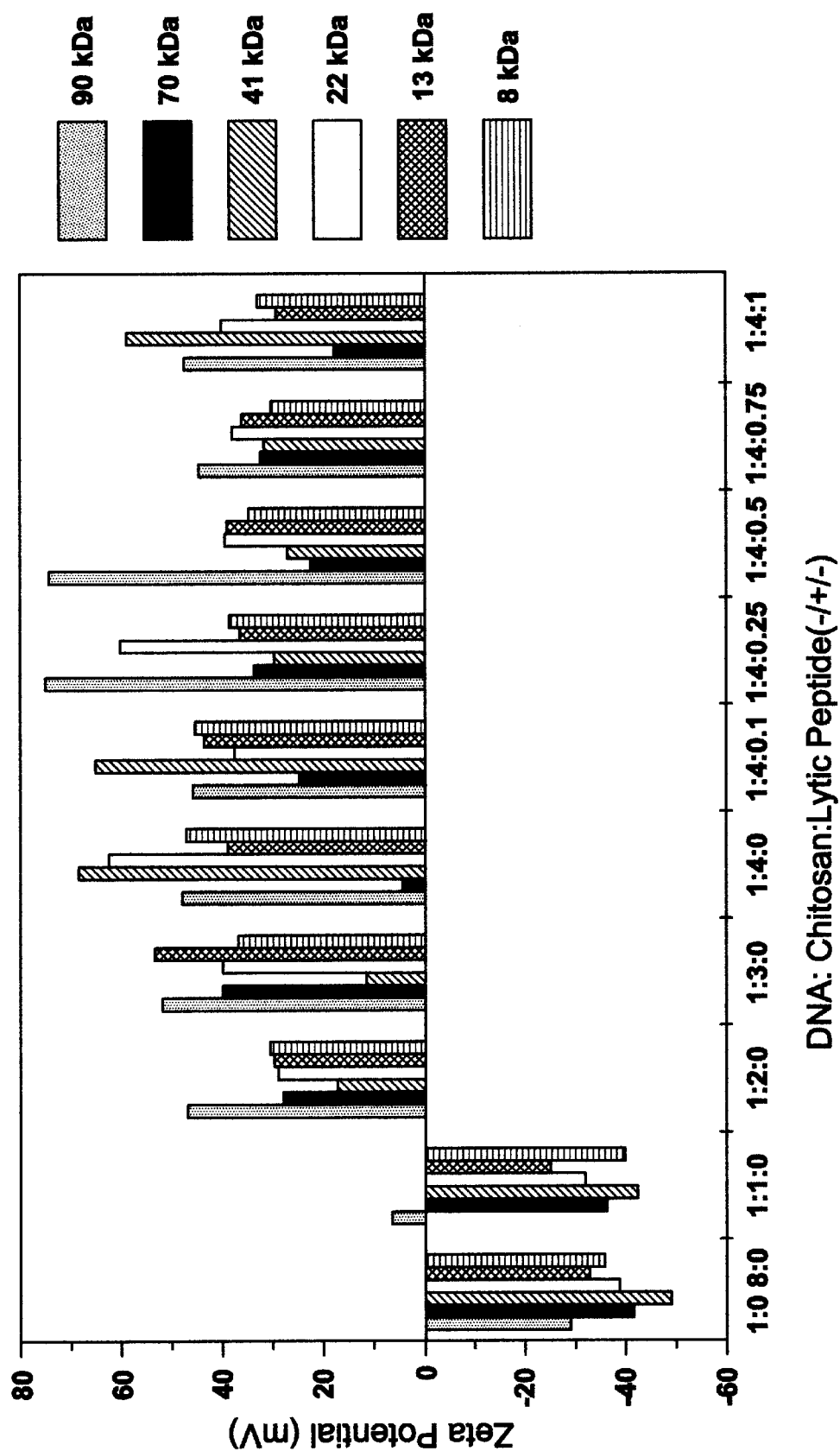
FIG. 7 shows the Zeta potential values of compositions made with chitosan-based compounds with and without the inclusion of a lytic peptide. The compositions were made in water with a DNA concentration of 200 μg/ml.

The zeta potential (i.e., the measure of the charge ratio) of compositions (e.g., of FIG. 6A) are shown in FIG. 7. In general, the increasing addition of chitosan and/or chitosan oligomers to the composition increased the net positive charge directly.

The addition of negatively charged lytic peptide to the composition decreased the positive charge of the complex proportionally. The observation of a net negative charge at the theoretical neutral charge ratio of 1:1 −/+ appears anomalous and could be due to incomplete charge neutralization as a result of increased solubility of these compositions.

Example 11

In Vivo Studies of Chitosan Complex

We assessed the ability of a chitosan composition to express a reporter gene in vivo in the intestinal mucosa of rabbits. Rabbits were anaesthetized and laparotomies performed, then chitosan-based compositions were administered either colonically or to the small intestine. The dose of formulated CMV-CAT used was 100 $\mu$g in 1 ml 10% lactose. To prevent leakage at the dosing site, the site was sealed with an adhesive and the abdominal cavity was closed with two layers of sutures. Rabbits were sacrificed by an overdose of pentobarbitone 72 hr after administration.

Tissues collected from the intestinally dosed rabbits were Peyer's Patches (PP1, PP2, PP3), enterocytes (ENT1, ENT2, ENT3), colon (COL), and mesenteric lymph nodes (MLN). PP1 and ENT1 were from regions proximal to the dosing site, PP2 and ENT2 were from regions median to the dosing site, and PP3 and ENT3 were from regions distal to the dosing site.

Tissues collected from colonically dosed rabbits were colon (COL1, COL2, COL3) and MLN. COL1 tissue was from regions proximal to the dosing site, COL2 was from regions median to the dosing site, and COL3 was from regions distal to the dosing site. The tissues COL and ENT were 1–1.5 $cm^2$ in size. The PP, COL, and ENT tissues were cut into two pieces and were snap frozen while the MLN tissues were snap frozen as one piece. Tissues were homogenized and extracted with 1 ml of extraction buffer and analyzed for CAT expression using an ELISA assay. The tissues were also analyzed for total protein content. Results are expressed as pg CAT/ug protein.

Chemiluminescent Detection Procedure

It is recommended that all assays are performed in triplicate. (1) Dilute Galacton™ (Galacton-plus™) substrate 100-fold with Galacto-Light™ Reaction Buffer Diluent to make Reaction Buffer. This mixture will remain stable for several months if stored uncontaminated at 4° C. It is recommended to only dilute the amount of substrate that will be used within a two month period. (2) Warm to room temperature the amount of Reaction Buffer required for the entire experiment. (3) Aliquot 2 to 20 $\mu$l of individual cell extracts into luminometer sample tubes. (The amount of cell extract required may vary depending on the amount of expression and the instrumentation used. Use 5 $\mu$l of extract for positive controls and 10 to 20 $\mu$l of extract for experiments with potentially low levels of enzyme. It is important to vary the concentrations of extract to keep the signal within the linear range of the assay) (4) Add 200 $\mu$l of Reaction Buffer to a luminometer cuvette and gently mix. Incubate at room temperature for 60 minutes. Incubations can be as short as 15 minutes, but the linear range of the assay may decrease. (Measurements are time dependent. Reaction Buffer should be added to sample extracts in the same time frame as they are counted on the luminometer. For example, if it takes 10 seconds to completely count a sample, then Reaction Buffer should be added to tubes every 10 seconds) (5) Place cuvette in a luminometer. Inject 300 $\mu$l of Accelerator. After a 2 to 5 second delay following injection, count the sample for 5 seconds. If manual injection is used, then the Accelerator should be added in the same consistent time frame as the Reaction Buffer is added. This is critical when using Galacton™.

Preparation of Controls

Positive Control

Add 1 $\mu$l of β-galactosidase (10 units/ml, Sigma Cat. No. G-5635 diluted in 0.1 M sodium phosphate pH 7.0, 1.0% BSA) to mock transfected cell extract equivalent to the volume of experimental cell extract used. Proceed with Chemiluminescent Detection Procedure.

Negative Control

Assay of volume of mock transfected cell extract equivalent to the volume of experimental cell extract used. Proceed with Chemiluminescent Detection Procedure.

Heat Inactivation of Endogenous β-galactosidase

Some cell lines may exhibit relatively high levels of endogenous β-galactosidase activity. This may lead to background which will decrease the overall sensitivity of the assay by lowering the signal to noise ratio. A procedure for heat inactivation of endogenous β-galactosidase activity has been described by Young et al., Anal. Biochem. 215:24–30 (1993), incorporated herein by reference in its entirety including any drawings or figures. A modified version of this protocol has also been described by Shaper et al., J. Biol. Chem. 269:25165–25171 (1994), incorporated herein by reference in its entirety including any drawings or figures, in which a cocktail of protease inhibitors is used in conjunction with the heat inactivation procedure for reducing β-galactosidase in tissue extracts.

Inactivation of β-Galactosidase Activity in Cell Extracts

The following procedures should be performed immediately prior to the Chemiluminescent Detection Procedure in the Preparation of Cell Extracts From Tissue Culture Section. (1) Following cell extract preparation, heat the extract to 48° C. for 50 minutes. (2) Proceed with Chemiluminescent Detection Procedure. (Although Young et al. suggest 50° C. for 60 minutes, heat inactivation at 48° C. for 50 minutes is suggested).

Inactivation of Endogenous β-Galactosidase Activity in Tissue Extracts (1) To the Galacto-Light™ lysis buffer, add PMSF to a final concentration of 0.2 mM and leupeptin to a final concentration of 5 $\mu$g/ml just before use. (2) Heat inactivate the extracts by heating at 48° C. for 60 minutes. (3) Proceed with Chemiluminescent Detection Procedure. (AEBSF (Sigma Cat. No. A-5938) may be used in place of PMSF (Sigma Cat. No. P-7626). AEBSF is a water soluble serine protease inhibitor).

A liquid scintillation counter may be used as a substitute for a luminometer, however, sensitivity may be lower Fulton, R., and B. Van Ness. Luminescent Reporter Gene Assays for Luciferase and β-galactosidase Using a Liquid Scintillation Counter. BioTechniques 14(5): 762–763(1993), incorporated herein by reference. Nguyen, V. T., M. Morange, and O. Bensaude. Firefly Luciferase Luminescence Assays Using Scintillation Counters for Quantitation in Transfected Mammalian Cells. Anal. Biochem. 171:404–408 (1988), incorporated herein by reference. The results are expressed as mean +/- S.E.M of Relative Light Unit, as indicative of b-galactosidase activity, per 100 ug muscle protein. When using a scintillation counter, it is necessary to turn off the coincident circuit in order to measure chemiluminescence directly. The manufacturer of the instrument should be contacted to determine how this is done. If it is not possible to turn off the coincident circuit, a linear relationship can be established by taking the square root of the counts per minute measured and subtracting the instrument background. Actual=(measured-instrument background)$^{1/2}$. Other methods of measuring a chemiluminescent signal as are known in the art may also be utilized.

EXAMPLE 12

In Vitro Transfection Using Chitosan/Nucleic Acid Complex

We assessed in vitro cell transfection using chitosan compositions depicted in FIG. 6A.

Rabbit synoviocytes(HIG-82) plated in 24-well plates (100,000 cells/well) were incubated overnight in DMEM supplemented with 10% FBS and with compositions prepared in water with and without the inclusion of varying amounts of lytic peptide. Final DNA concentration was 200 μg/ml. Media was removed from the cells (40–60% confluent) and fresh media (DMEM with 10% FBS) was added prior to the addition of the compositions. For all compositions, 50 ml (10 μg CMV-Bgal) was added. Cells were incubated with the compositions for 48 hours then removed, and washed with PBS (pH 7.4). Galacto-Light™ cell lysate solution was added including 1 mm DTT. A chemiluminescence detection system for B-galactosidase (Galacto-Light™) was used to determine the Relative Light Units (RLU) per mg cell lysate protein (RLU/mg protein). Total protein content in cell lysates were measured with a Coomassie Blue G250-based assay (Bio-Rad; Hercules, Calif.).

Figure 8:
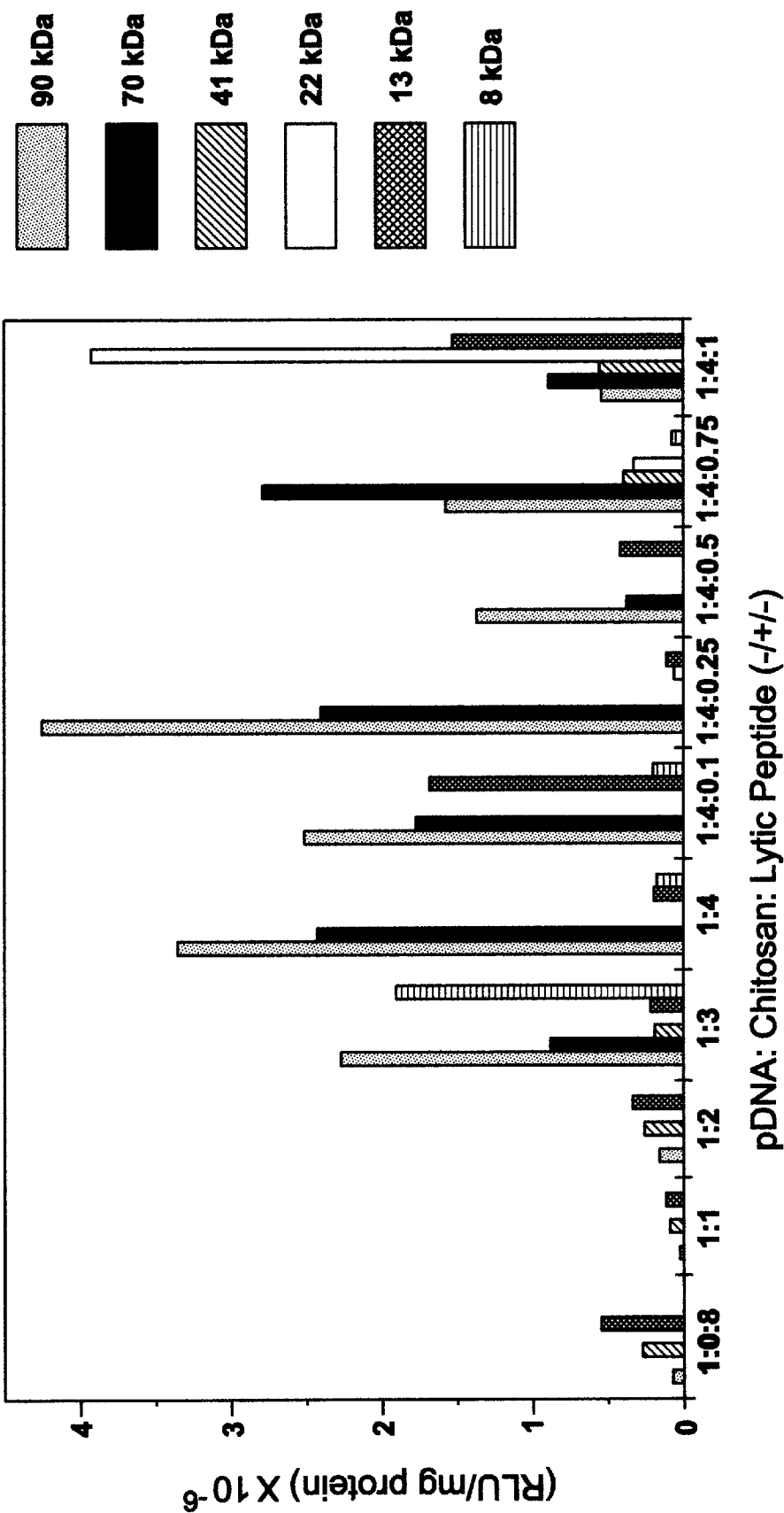
FIG. 8 shows the results of in vitro cell transfection of HIG-82 (rabbit synovioctyes) in the presence of 10% FBS. The transfection efficiency (in RLU/μg protein) is shown as a function of chitosan molecular weight and the inclusion of various amounts of a lytic peptide. 10 ug of formulated CMV-Bgal was added to the cells and the cells were harvested after 48 hours.

The efficiency of cell transfection of the compositions is shown in FIG. 8. The transfection efficiency of the composition was positively correlated with increasing positive charge.

However, the transfection efficiency correlated poorly with the molecular weight of the chitosan used.

Addition of lytic peptide to the composition increased the transfection efficiency only with the addition of small amounts of large molecular weight chitosan (90 kDa and 70 kDa) or the addition of large amounts of smaller molecular weight chitosans. This effect may be related to the size of the compositions and the inherent stability in solution. The interaction of the compositions with 10% FBS may also be a contributing factor.

Methods of Preparation of Cell Extracts From Tissue Culture Cells (1) Aliquot the required amount of Lysis Solution. Add fresh DTT to 1 mM. (2) Rinse cells 2 times with 1×Phosphate Buffered Saline (PBS). (3) Add Lysis Solution to cover the cells (250 μl of Lysis Buffer for a 60 mm culture plate should be adequate). (4) Detach cells from culture plate using a rubber policeman or equivalent. Non-adherent cells should be pelleted and lysis buffer should be added sufficient to cover the cells. The cells should then be resuspended in the lysis buffer by pipetting. (5) Transfer cells to a microfuge tube and centrifuge for 2 minutes to pellet any debris. (6) Transfer supernatant to a fresh microfuge tube. Cell extracts may be used immediately or frozen at −70° C. for future use.

EXAMPLE 13

Oral Administration of Chitosan/Nucleic Acid Complex

A preferred route of administration of chitosan-based compositions is orally. Oral administration may best utilize the beneficial properties of chitosan (as discussed above). Oral administration permits chitosan-based compositions to be taken up by various cell types throughout the entire length of the alimentary canal thereby allowing the expression of therapeutic products locally and/or systemically. Chitosan administration has been examined in the gut to determine its bioadhesive properties. Additionally, chitosan has been approved by the FDA as a food additive.

We assessed the ability of chitosan-based compositions to express a reporter gene (i.e., chloramphenicol acetyltransferase; in a CAT assay) in vivo after oral administration. Lyophilized and rehydrated chitosan-based compositions (e.g., 90 kDa chitosan like those in FIG. 5) were dosed in the upper small intestine or colonically in rabbits. Tissues were examined for gene expression after administration as in example 12. Expression was measured 72 hours after administration.

The results are shown in Tables 3 & 4.

TABLE 3

Summary of Expressed CAT in Tissue Extracts of Rabbits Dosed in the Upper Small Intestine with DNA:Chitosan:Lytic Peptide Formulation

| Formulation | Region | Rabbit 1 | Rabbit 2 | Rabbit 3 | Rabbit 4 | Mean pg/mg | S.D. pg/mg |
|---|---|---|---|---|---|---|---|
| Chitosan:LP | PP1 | 0.00 | 0.00 | 0.00 | 0.00 | 0.00 | 0.00 |
| | PP2 | 0.00 | 0.00 | 0.00 | 0.00 | 0.00 | 0.00 |
| | PP3 | 6.12 | 5.01 | 0.00 | 5.83 | 4.24 | 2.87 |

TABLE 3-continued

|  |  |  |  |  |  |  |  |
|---|---|---|---|---|---|---|---|
|  | ENT1 | 1.45 | 0.00 | 8.10 | 6.62 | 4.04 | 3.92 |
|  | ENT2 | 0.00 | 4.50 | 0.00 | 9.60 | 3.52 | 4.57 |
|  | ENT3 | 6.16 | 0.00 | 11.41 | 4.32 | 5.47 | 4.72 |
|  | Col | 0.00 | 0.00 | 0.00 | 0.00 | 0.00 | 0.00 |
|  | MLN | 0.00 | 0.00 | 3.68 | 10.96 | 3.66 | 5.17 |

|  | Region | Rabbit 5 | Rabbit 6 | Mean pg/mg | S.D. pg/mg |
|---|---|---|---|---|---|
| DNA in water | PP3 | 0.000 | 0.000 | 0.000 | 0.000 |
|  | ENT1 | 0.000 | 0.000 | 0.000 | 0.000 |
|  | MLN | 0.000 | 0.000 | 0.000 | 0.000 |

TABLE 4

Summary of Expressed CAT in Tissue Extracts of Rabbits Dosed Colonically with DNA: Chitosan:Lytic Peptide Formulation

| Formulation | Region | Rabbit 7 | Rabbit 8 | Rabbit 9 | Rabbit 10 | Mean pg/mg | S.D. pg/mg |
|---|---|---|---|---|---|---|---|
| Chitosan:LP | Col 1 | 0.00 | 0.00 | 0.00 | 6.30 | 1.58 | 3.20 |
|  | Col 2 | 0.00 | 0.00 | 7.47 | 6.82 | 3.57 | 4.13 |
|  | Col 3 | 0.00 | 0.00 | 0.00 | 0.00 | 0.00 | 0.00 |
|  | MLN | 5.97 | 10.11 | 12.14 | 0.00 | 7.06 | 5.36 |

|  | Region | Rabbit 11 | Rabbit 12 | Mean pg/mg | S.D. pg/mg |
|---|---|---|---|---|---|
| DNA in water | Col 2 | 0.000 | 0.000 | 0.000 | 0.000 |
|  | MLN | 0.000 | 0.000 | 0.000 | 0.000 |

The results demonstrate that the chitosan-based compositions using a CMV-CAT expression vector delivered a functioning CMV-CAT expression vector into cells while controls (i.e., naked DNA CMV-CAT expression vector in water) showed no expression in any tissues in any region.

One rabbit administered the chitosan composition demonstrated expression of the CAT reporter gene in almost all the tissues examined except for PP1 and PP2 Col (when dosed in the upper small intestine) or Col 3 (when dosed colonically).

Since cell turnover in the gut is known to be rapid and extensive, we believe that significantly higher CAT expression would have been observed had tissue samples been examined at earlier time points than 72 hours after administration. Nevertheless, these results demonstrate the efficacy of gene delivery and gene expression using the chitosan-based compositions of the present invention.

Enzyme-Linked Immunoassay (ELISA) for Chloramphenicol Acetyltransferase (CAT) in Rodent Lungs Reagents
A. CAT ELISA Kit: Boehringer-Mannhiem, Cat#1363727
CAT enzyme (50 ng)
Anti-CAT-digoxigenin
Anti-DIG-peroxidase
Substrate buffer
ABTS substrate
Substrate Enhancer
Wash Buffer
Sample buffer
Microtiter plate modules (8-wells)
plastic film plate covers B. Samples in buffer compatible with ELISA (TEN buffer: 50 mM Tris pH 7.5–8.0, 1 mM EDTA, 150 mM NaCl, up to 1% Triton X-100)
Sample Preparation Homogenization buffer: Samples homogenized in 50 mM Tris-Cl pH8.0, 1.0 mM EDTA, 150 mM NaCl, 0.5% Triton X-100, 10 $\mu$M Leupeptin, 1.0 $\mu$M Pepstatin A, and 0.25 mM PMSF.

Tissue samples are snap frozen in separate homogenization tubes. Thaw samples on ice. Spin samples briefly to pellet tissue into beads. If tissue exceeds 50% tube capacity after pelleting, divide equally the lung into two tubes. Tubes are filled to 1.8 ml with cold homogenization buffer; cap tubes tightly! Keep samples on ice.

An alternative method of the above is: tissue samples are snap frozen in separate homogenization tubes. Thaw samples on ice. Spin samples briefly to pellet tissue into beads. Tubes are filled to 1.0 ml with cold homogenization buffer; cap tubes tightly! Keep samples on ice.

Using the Biospec mini-beadbeater (follow manufacturer's instructions), homogenize samples to completion (1–4 minutes) @ 4° C. Spin samples @ 4° C. for 15 minutes. Transfer supernatant to fresh tube; keep on ice. (Note: if samples are excessively turbid, spin again for an additional 15 minutes).
Prepare Sample Template Using a 96 well microtiter plate, aliquot 150 $\mu$l homogenate to well. Keep plate on ice. Aliquot 150 $\mu$l H$_2$O to each well (1:1); mix well; keep on ice. (Note: this template will be used for both the CAT ELISA and the protein concentration assay. After setting up CAT ELISA, save the plate. The remaining 100 $\mu$l of diluted sample is used for protein determination)
Assay 1. Rehydrate needed amount of anti-CAT antibody pre-coated microtiter plate strips with sample buffer for 5 minutes @ RT.

2. Following rehydration, discard the solution and wells on paper towel to remove excess liquid.

3a. Pipette 200 μl of CAT standards, in duplicate, prepared as described below. For standard curve, make 1 ng/ml CAT in sample buffer (follow manufacturer's instructions) make 500 μl of serial two-fold dilutions of 1 ng/ml solution.

| final conc. (pg/200 ul) = | diluted CAT @ | CAT (pg/ml) + | Sample buffer |
|---|---|---|---|
| 100 | 500 μl | 1000 | 500 μl |
| 50 | 500 μl | 500 | 500 μl |
| 25 | 500 μl | 250 | 500 μl |
| 12.5 | 500 μl | 125 | 500 μl |
| 6.25 | 500 μl | 62.5 | 500 μl |
| 3.13 | 500 μl | 31.3 | 500 μl |
| 1.56 | 500 μl | 15.6 | 500 μl |
| 0 | — | — | 500 μl |

3b. Pipette 100 ul of 1:1 diluted tissue sample in to duplicate into wells. Add 100 ul CAT ELISA buffer to wells containing diluted tissue sample. Standards and sample should now have 200 ul/well. Cover plate with plastic film, incubate @ 37 deg C. for 1 hr.

4. Using Dynatech Laboratories Ultrawash Plus plate washer, (setting 8116), wash plate with 50 mM Tris-Cl pH7.6, 1.0 mM EDTA, 150 mM NaCl, 0.1% Tween-20.

5. Add 200 μl of anti-CAT-DIG antibody (1:100 dilution in sample buffer) to wells, incubate 1 hr @ 37 deg C.

6. Wash wells as in step 4.

7. Add 200 μl of anti-DIG-peroxidase (75 ul into 9.925 ml of sample buffer) to wells, incubate 1 hr @ 37 deg C.

8. Wash well as in step 4.

9. Add 200 μl of peroxidase substrate, prepared using manufacturers instructions (ABTS) in buffer. Note: add substrate enhancer @ 1 mg/ml to ABTS solution if low concentrations of CAT are expected.

10. Read plate @ OD 405. Calculate concentration of CAT in standards using OD values obtained from linear portion of standard curve. The time of OD readings should empirically determined to place sample values on linear portion of standard curve.

One skilled in the art would readily appreciate that the present invention is well adapted to carry out the objects and obtain the ends and advantages mentioned, as well as those inherent therein. The chitosan/nucleic acid complex along with the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A method of making a composition comprising: (a) a chitosan-based compound; and (b) a nucleic acid or an oligonucleotide, wherein said composition delivers said nucleic acid or said oligonucleotide into a cell, wherein said composition has a net negative charge ratio, comprising the steps of:

(a) exposing said chitosan-based compound to an acid;
    (b) filtering the acid treated product of step (a);
    (c) adding the acid treated and filtered product of step (b) to said nucleic acid or said oligonucleotide in an acceptable pharmaceutical carrier.

2. The method of claim 1, wherein said nucleic acid or said oligonucleotide is present in a concentration ranging from 10 to 4,000 μg per ml of said acceptable pharmaceutical carrier.

3. The method of claim 1, wherein said nucleic acid or said oligonucleotide is present in a concentration ranging from 100 to 400 μg per ml of said acceptable pharmaceutical carrier.

4. The method of claim 1, wherein said acid is acetic acid.

5. The method of claim 4, wherein said acetic acid is present in a concentration between 0.2% v/v and 1.0% v/v.

6. A composition comprising:
    (a) a chitosan-based compound;
    (b) a cryoprotectant; and
    (c) a nucleic acid or an oligonucleotide, wherein said composition delivers said nucleic acid or said oligonucleotide into a cell, and wherein said composition has a net negative charge ratio.

7. The composition of claim 6, wherein said chitosan-based compound is chitin.

8. The composition of claim 6, wherein said chitosan-based compound is a chitosan monomer.

9. The composition of claim 6, wherein said chitosan-based compound is a chitosan oligomer.

10. The composition of claim 6, wherein said chitosan-based compound forms a complex with said nucleic acid or said oligonucleotide.

11. The composition of claim 6, wherein said chitosan-based compound condenses said nucleic acid.

12. The composition of claim 6, wherein said composition has a diameter between 15 nm and 10,000 nm.

13. The composition of claim 6, wherein said composition has a diameter between 15 nm and 1,000 nm.

14. The composition of claim 6, wherein said composition has a pH in the range of 4.0 to 8.0.

15. The composition of claim 6, wherein said chitosan-based compound has a molecular weight in the range of 5 kDA to 1000 kDa.

16. The composition of claim 6, wherein said chitosan-based compound has a molecular weight in the range of 5 kDA to 600 kDa.

17. The composition of claim 6, wherein said nucleic acid of said composition is expressed inside of said cell.

18. The composition of claim 6, wherein said nucleic acid of said composition is delivered inside of said cell to function as an antisense molecule.

19. The composition of claim 6, wherein said composition is lyophilized, stored, rehydrated, delivered to a cell, whereby said nucleic acid or said oligonucleotide is expressed inside of said cell.

20. A method of delivering a nucleic acid or oligonucleotide to a cell, comprising the step of delivering the composition of claim 6 to said cell.

21. The method of claim 20, wherein said cell is in vitro.

22. The method of claim 20, wherein said cell is in vivo and said delivering step comprises administering said composition to an organism.

23. The method of claim 20, wherein said cell has been removed from a living organism.

* * * * *